(12) United States Patent
Pilon et al.

(10) Patent No.: US 9,394,349 B2
(45) Date of Patent: Jul. 19, 2016

(54) MODIFICATION AND COMPOSITIONS OF HUMAN SECRETOGLOBIN PROTEINS

(71) Applicant: Clarassance, Inc., Rockville, MD (US)

(72) Inventors: Aprile L. Pilon, Rockville, MD (US);
Humcha K. Hariprakasha, Rockville, MD (US); Richard S. Clayton, Rockville, MD (US); Melissa E. Winn, Rockville, MD (US)

(73) Assignee: Therabron Therapeutics, Inc., Rockville, MD (US)

( * ) Notice: Subject to any disclaimer, the term of this patent is extended or adjusted under 35 U.S.C. 154(b) by 0 days.

(21) Appl. No.: 13/843,773

(22) Filed: Mar. 15, 2013

(65) Prior Publication Data
US 2014/0275477 A1 Sep. 18, 2014

(51) Int. Cl.
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| C07K 14/47 | (2006.01) |

(52) U.S. Cl.
CPC ..................................... C07K 14/47 (2013.01)

(58) Field of Classification Search
CPC ................................ C07K 14/47; A61K 38/00
See application file for complete search history.

(56) References Cited

U.S. PATENT DOCUMENTS

| 6,953,666 | B1 | 10/2005 | Kinkade |
| 2001/0029025 | A1 | 10/2001 | Dreyfuss |
| 2003/0008816 | A1 | 1/2003 | Pilon |
| 2004/0047857 | A1* | 3/2004 | Pilon et al. ................. 424/130.1 |
| 2008/0063626 | A1 | 3/2008 | Ding |
| 2009/0004684 | A1 | 1/2009 | Maier |

FOREIGN PATENT DOCUMENTS

WO    WO 2011047065 A1 *  4/2011

OTHER PUBLICATIONS

Vilaseca M et al. "Stepwise and Convergent Approaches to the Synthesis of the Uteroglobin Monomer, a 70 Amino Acid Peptide" Peptides 1996, Proceedings of the European Symposium. Published 1998.*
Levine et al. "Safety, Pharmacokinetics, and Anti-Inflammatory Effects of Intratracheal Recombinant Human Clara Cell Protein in Premature Infants with Respiratory Distress Syndrome" Pediatric Research 58:15-21. Published 2005.*
PCT Search Report and Written Opinion in PCT/US2014/030117 dated Sep. 29, 2014.
PCT International Preliminary Report on Patentability in PCT/US2014/030117 dated Mar. 2, 2015.
Levine, et al. Safety, Pharmacokinetics, and Anti-inflammatory Effects of Intratracheal Recombinant Human Clara Cell Protein in Premature Infants with Respiratory Distress Syndrome; Pediatric Research (Jul. 2005) 58, 15-21.
Antico, G., M. W. Lingen, A. Sassano, J. Melby, R. W. Welch, S. Fiore, A. L. Pilon and L. Miele. "Recombinant human uteroglobin/CC10 inhibits the adhesion and migration of primary human endothelial cells via specific and saturable binding to fibronectin." J Cell Physiol 207(2): 553-561 (Dec. 2005).
Arias-Martinez, J., M. Palacios-Sanchez, D. Delgado-Franco, J. Guzman-Barcenas, E. Garcia-Latorre, L. Zhang and C. Irles. "Clara cell protein expression in human neonates during respiratory distress syndrome." Cell Physiol Biochem 29(5-6): 753-760 (Mar. 2012).
Barnes, H. J., L. Nordlund-Moller, M. Nord, J. Gustafsson, J. Lund and M. Gillner. "Structural basis for calcium binding by uteroglobins." J Mol Biol 256(2): 392-404 (Nov. 1995).
Berlett, B. S. and E. R. Stadtman. "Protein oxidation in aging, disease, and oxidative stress." J Biol Chem 272(33): 20313-20316 (Aug. 1997).
Cai, Z. and L. J. Yan. "Protein Oxidative Modifications: Beneficial Roles in Disease and Health." J Biochem Pharmacol Res 1(1): 15-26 (Mar. 2013).
Callebaut, I., A. Poupon, R. Bally, J. P. Demaret, D. Housset, J. Delettre, P. Hossenlopp and J. P. Mornon. "The uteroglobin fold." Ann N Y Acad Sci 923: 90-112 (Jan. 2000).
Chalker, J. M., L. Lercher, N. R. Rose, C. J. Schofield and B. G. Davis. "Conversion of cysteine into dehydroalanine enables access to synthetic histones bearing diverse post-translational modifications." Angew Chem Int Ed Engl 51(8): 1835-1839 (Sep. 2011).
Davies, K. J., M. E. Delsignore and S. W. Lin. "Protein damage and degradation by oxygen radicals. II. Modification of amino acids." J Biol Chem 262(20): 9902-9907 (Jul. 1987).
Folk, J. E. "Mechanism of action of guinea pig liver transglutaminase. VI. Order of substrate addition." J Biol Chem 244(13): 3707-3713 (Aug. 1967).
Guptasarma, P., D. Balasubramanian, S. Matsugo and I. Saito. "Hydroxyl radical mediated damage to proteins, with special reference to the crystallins." Biochemistry 31(17): 4296-4303 (Jul. 1991).

(Continued)

*Primary Examiner* — Christina Bradley
*Assistant Examiner* — Zachary J Miknis
(74) *Attorney, Agent, or Firm* — Henry J. Cittone; Cittone & Chinta LLP

(57) ABSTRACT

Novel compositions of recombinant human CC10 protein have been generated by chemically modifying the pure protein in vitro. Several new synthetic preparations containing isoforms of chemically modified CC10 have been generated by processes that utilize reactive oxygen species and reactive nitrogen species. These preparations contain novel isoforms of CC10 which have been characterized with enhanced or altered biological properties compared to the unmodified protein. Preparations containing novel isoforms may be used as standards to identify and characterize naturally occurring isoforms of native CC10 protein from blood or urine and ultimately to measure new CC10-based biomarkers to assess patient disease status. These preparations may also be used to treat respiratory, autoimmune, inflammatory, and other medical conditions that are not effectively treated with the unmodified protein.

180 Claims, 23 Drawing Sheets

(56) References Cited

OTHER PUBLICATIONS

Hard, T., H. J. Barnes, C. Larsson, J. A. Gustafsson and J. Lund. "Solution structure of a mammalian PCB-binding protein in complex with a PCB." Nat Struct Biol 2(11): 983-989 (Nov. 1995).
Hawkins, C. L., D. I. Pattison and M. J. Davies. "Hypochlorite-induced oxidation of amino acids, peptides and proteins." Amino Acids 25(3-4): 259-274 (Jan. 2003).
Hazen, S. L., F. F. Hsu and J. W. Heinecke. "p-Hydroxyphenylacetaldehyde is the major product of L-tyrosine oxidation by activated human phagocytes. A chloride-dependent mechanism for the conversion of free amino acids into reactive aldehydes by myeloperoxidase." J Biol Chem 271(4): 1861-1867 (Sep. 1995).
Henderson, J. P., J. Byun, M. V. Williams, D. M. Mueller, M. L. McCormick and J. W. Heinecke. "Production of brominating intermediates by myeloperoxidase. A transhalogenation pathway for generating mutagenic nucleobases during inflammation." J Biol Chem 276(11): 7867-7875 (Nov. 2000).
Jeon, J. H. and I. G. Kim. "Role of protein modifications mediated by transglutaminase 2 in human viral diseases." Front Biosci 11: 221-231 (Jan. 2006).
Klug, J., H. M. Beier, A. Bernard, B. S. Chilton, T. P. Fleming, R. I. Lehrer, L. Miele, N. Pattabiraman and G. Singh. "Uteroglobin/Clara cell 10-kDa family of proteins: nomenclature committee report." Ann N Y Acad Sci 923: 348-354 (2000).
Lesort, M., J. Tucholski, M. L. Miller and G. V. Johnson. "Tissue transglutaminase: a possible role in neurodegenerative diseases." Prog Neurobiol 61(5): 439-463 (Aug. 1999).
Lindahl, M., K. Irander, C. Tagesson and B. Stahlbom. "Nasal lavage fluid and proteomics as means to identify the effects of the irritating epoxy chemical dimethylbenzylamine." Biomarkers 9(1): 56-70 (Sep. 2003).
Lindahl, M., J. Svartz and C. Tagesson. "Demonstration of different forms of the anti-inflammatory proteins lipocortin-1 and Clara cell protein-16 in human nasal and bronchoalveolar lavage fluids." Electrophoresis 20(4-5): 881-890 (Sep. 1998).
Lorand, L. and R. M. Graham. "Transglutaminases: crosslinking enzymes with pleiotropic functions." Nat Rev Mol Cell Biol 4(2): 140-156 (Feb. 2003).
Madian, A. G. and F. E. Regnier. "Proteomic identification of carbonylated proteins and their oxidation sites." J Proteome Res 9(8): 3766-3780 (Aug. 2010).
Mantile, G., L. Miele, E. Cordella-Miele, G. Singh, S. L. Katyal and A. B. Mukherjee. "Human Clara cell 10-kDa protein is the counterpart of rabbit uteroglobin." J Biol Chem 268(27): 20343-20351 (Apr. 1993).
Mukherjee, A. B., E. Cordella-Miele, T. Kikukawa and L. Miele. "Modulation of cellular response to antigens by uteroglobin and transglutaminase." Adv Exp Med Biol 231: 135-152 (Jan. 1988).
Mukherjee, A. B., G. C. Kundu, G. Mantile-Selvaggi, C. J. Yuan, A. K. Mandal, S. Chattopadhyay, F. Zheng, N. Pattabiraman and Z. Zhang. "Uteroglobin: a novel cytokine?" Cell Mol Life Sci 55(5): 771-787 (Dec. 1998).
Mukherjee, A. B., Z. Zhang and B. S. Chilton. "Uteroglobin: a steroid-inducible immunomodulatory protein that founded the Secretoglobin superfamily." Endocr Rev 28(7): 707-725 (Oct. 2007).
Nagy, P., A. J. Kettle and C. C. Winterbourn. "Superoxide-mediated formation of tyrosine hydroperoxides and methionine sulfoxide in peptides through radical addition and intramolecular oxygen transfer." J Biol Chem 284(22): 14723-14733 (May 2009).
Nemes, Z., L. N. Marekov, L. Fesus and P. M. Steinert. "A novel function for transglutaminase 1: attachment of long-chain omega-hydroxyceramides to involucrin by ester bond formation." Proc Natl Acad Sci U S A 96(15): 8402-8407 (Jul. 1999).
Nicolas, E., C. Ferrer, L. Taboada and E. Giralt. "Coupe du roi bisection of proteins. Spontaneous tetramerization of two peptides that span the sequence of the rabbit uteroglobin monomer." J Am Chem Soc 127(50): 17719-17733 (Jun. 2005).
Ottaviano, F. G., D. E. Handy and J. Loscalzo. "Redox regulation in the extracellular environment." Circ J 72(1): 1-16 (Oct. 2007).
Pedruzzi, E., M. Fay, C. Elbim, M. Gaudry and M. A. Gougerot-Pocidalo. "Differentiation of PLB-985 myeloid cells into mature neutrophils, shown by degranulation of terminally differentiated compartments in response to N-formyl peptide and priming of superoxide anion production by granulocyte-macrophage colony-stimulating factor." Br J Haematol 117 (3): 719-726 (Dec. 2001).
Peter, W., R. Dunkel, P. F. Stouten, G. Vriend, M. Beato and G. Suske. "Interchain cysteine bridges control entry of progesterone to the central cavity of the uteroglobin dimer." Protein Eng 5(4): 351-359 (Jan. 1992).
Ramsay, P. L., F. J. DeMayo, S. E. Hegemier, M. E. Wearden, C. V. Smith and S. E. Welty. "Clara cell secretory protein oxidation and expression in premature infants who develop bronchopulmonary dysplasia." Am J Respir Crit Care Med 164(1): 155-161 (Aug. 2000).
Shacter, E. "Quantification and significance of protein oxidation in biological samples." Drug Metab Rev 32(3-4): 307-326 (Jan. 2000).
Shao, B., A. Belaaouaj, C. L. Verlinde, X. Fu and J. W. Heinecke. "Methionine sulfoxide and proteolytic cleavage contribute to the inactivation of cathepsin G by hypochlorous acid: an oxidative mechanism for regulation of serine proteinases by myeloperoxidase." J Biol Chem 280(32): 29311-29321 (Apr. 2005).
Stadtman, E. R. and B. S. Berlett. "Fenton chemistry. Amino acid oxidation." J Biol Chem 266(26): 17201-17211 (Mar. 1991).
Stadtman, E. R., J. Moskovitz, B. S. Berlett and R. L. Levine. "Cyclic oxidation and reduction of protein methionine residues is an important antioxidant mechanism." Mol Cell Biochem 234-235(1-2): 3-9 (Jan. 2002).
Thomas, E. L., M. B. Grisham and M. M. Jefferson. "Preparation and characterization of chloramines." Methods Enzymol 132: 569-585 (Jan. 1986).
Tien, M., B. S. Berlett, R. L. Levine, P. B. Chock and E. R. Stadtman. "Peroxynitrite-mediated modification of proteins at physiological carbon dioxide concentration: pH dependence of carbonyl formation, tyrosine nitration, and methionine oxidation." Proc Natl Acad Sci U S A 96(14): 7809-7814 (May 1999).
Umland, T. C., S. Swaminathan, W. Furey, G. Singh, J. Pletcher and M. Sax. "Refined structure of rat Clara cell 17 kDa protein at 3.0 a resolution." J Mol Biol 224(2): 441-448 (Nov. 1991).
Umland, T. C., S. Swaminathan, G. Singh, V. Warty, W. Furey, J. Pletcher and M. Sax. "Structure of a human Clara cell phospholipid-binding protein-ligand complex at 1.9 a resolution." Nat Struct Biol 1(8): 538-545 (Aug. 1994).
van Dalen, C. J., C. C. Winterbourn, R. Senthilmohan and A. J. Kettle. "Nitrite as a substrate and inhibitor of myeloperoxidase. Implications for nitration and hypochlorous acid production at sites of inflammation." J Biol Chem 275(16): 11638-11644 (Dec. 1999).
Winterbourn, C. C., M. B. Hampton, J. H. Livesey and A. J. Kettle. "Modeling the reactions of superoxide and myeloperoxidase in the neutrophil phagosome: implications for microbial killing." J Biol Chem 281(52): 39860-39869 (Jun. 2006).
Yan, L. J. and M. J. Forster. "Chemical probes for analysis of carbonylated proteins: a review." J Chromatogr B Analyt Technol Biomed Life Sci 879(17-18): 1308-1315 (Jan. 2011).
Yan, L. J., W. C. Orr and R. S. Sohal. "Identification of oxidized proteins based on sodium dodecyl sulfate-polyacrylamide gel electrophoresis, immunochemical detection, isoelectric focusing, and microsequencing." Anal Biochem 263(1): 67-71 (Jan. 1998).
Yang, C., J. Wang, A. N. Krutchinsky, B. T. Chait, J. D. Morrisett and C. V. Smith. "Selective oxidation in vitro by myeloperoxidase of the N-terminal amine in apolipoprotein B-100." J Lipid Res 42(11): 1891-1896 (Jan. 2001).
Yang, C. Y., Z. W. Gu, M. Yang, S. N. Lin, A. J. Garcia-Prats, L. K. Rogers, S. E. Welty and C. V. Smith. "Selective modification of apoB-100 in the oxidation of low density lipoproteins by myeloperoxidase in vitro." J Lipid Res 40(4): 686-698 (Feb. 1998).

* cited by examiner

Figure 1
Amino acid sequences of mature human secretoglobins

| Protein | Amino acid sequence |
|---|---|
| SCGB1A1 (CC10) | SEQ ID NO 1: EICPSFQRVIETLLMDTPSSYEAAMELFSPDQDMREAGAQLKKLVDTLPQKPRESIIKLMEKIAQSSLCN |
| SCGB3A1 | SEQ ID NO 2: AAFLVGSAKPVAQPVAALESAAEAGAGTLANPLGTLNPLKLLLSSLGIPVNHLIEGSQKCVAELGPQAVGAVKALKALLGALTVFG |
| SCGB3A2 | SEQ ID NO 3: AFLINKVPLPVDKLAPLPLDNILPFMDPLKLLLKTLGISVEHLVEGLRKCVNELGPEASEAVKKLLEALSHLV |
| SCGB2A1 | SEQ ID NO 4: SGCKLLEDMVEKTINSDISIPEYKELLQEFIDSDAAAEAMGKFKQCFINQSHRTLKNFGLMMHTVYDSIWCNMKSNMKLLMVLMLAALLLHCYAD |
| SCGB2A2 | SEQ ID NO 5: SGCPLLENVISKTINPQVSKTEYKELLQEFIDDNATTNAIDELKECFLNQTDETLSNVEVFMQLIYDSSLCDLFMKLLMVLMLAALSQHCYAG |
| SCGB1D1 | SEQ ID NO 6: VVCQALGSEITGFLLAGKPVFKFQLAKFKAPLEAVAAKMEVKKCVDTMAYEKRVLITKTLGKIAEKCDRMRLSVCLLLLTLALCCYRANA |
| SCGB1D2 | SEQ ID NO 7: EFCPALVSELLDFFFISEPLFKLSLAKFDAPPEAVAAKLGVKRCTDQMSLQKRSLIAEVLVKILKKCSVMKLSVCLLLVTLALCCYQANA |
| SCGB1D4 | SEQ ID NO 8: LCCYQAHALVCPAVASEITVFLFLSDAAVNLQVAKLNPPEALAAKLEVKHCTDQISFKKRLSLKKSWWKMRLSVCLLMVSLA |

Figure 2: HPLC analysis of NaOCl oxidation products
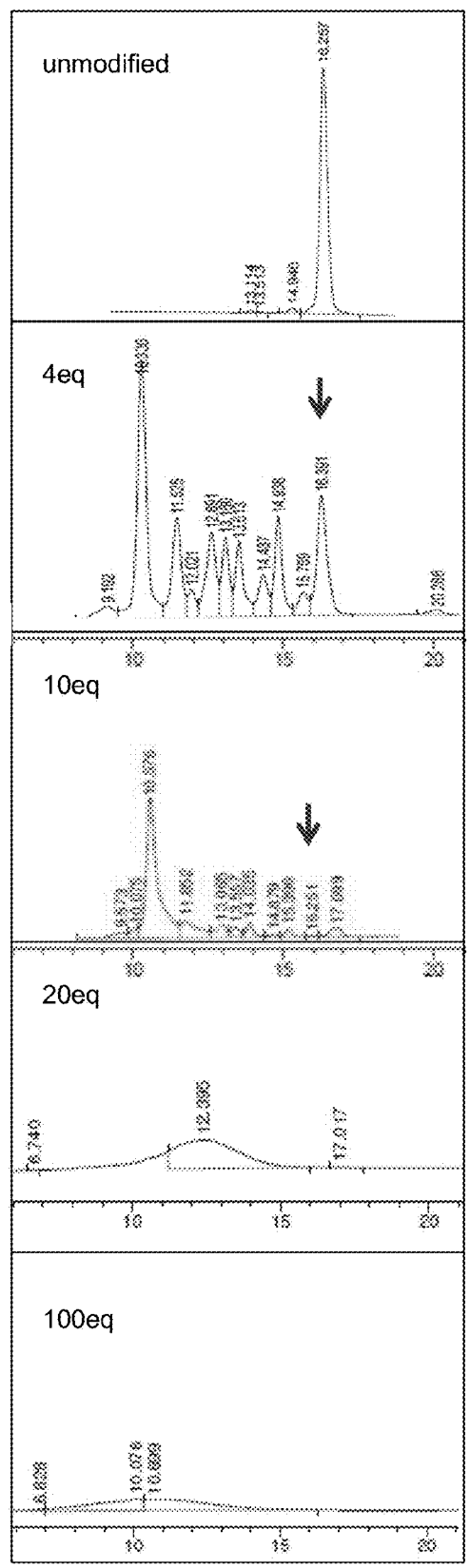

SDS-PAGE of rhCC10 NaOCl reactions 1. marker
2. rhCC10
3. 10 eq NaOCl
4. 20 eq
5. 40 eq
6. 60 eq
7. 80 eq
8. 100 eq
9. 5 eq Isoelectric focusing of rhCC10 NaOCl reactions 1. IEF marker
2. rhCC10
3. 10 eq NaOCl
4. 20 eq
5. 40 eq
6. 60 eq
7. 80 eq
8. 100 eq
9. 2 eq
10. 5 eq Western blot of IEF gel of rhCC10 NaOCl reactions using anti-rhCC10 antibody 1. Marker
2. rhCC10
3. 5 eq NaOCl in water (5.5 mg/mL)
4. 2 eq NaOCl in buffer(1.0 mg/mL)
5. 10 eq NaOCl in buffer(1.0 mg/mL)
6. 20 eq NaOCl in buffer(1.0 mg/mL)

Western blot of DNPH-treated rhCC10 NaOCl reactions
using anti-DNP antibody

|  | | Amount loaded |
|---|---|---|
| 1. | Marker | |
| 2. | 50 ng MPO+ 50 eq H$_2$O$_2$ | 10 mcg |
| 3. | 2 eq mCPBA in water (0.5 mg/mL) | 10 mcg |
| 4. | 5 eq NaOCl in water (5.5 mg/mL) | 10 mcg |
| 5. | 5 eq NaOCl in water (1.4 mg/mL) | 5 mcg |
| 6. | 5 eq NaOCl in buffer (2.7 mg/mL) | 5 mcg |
| 7. | 5 eq NaOCl in buffer (0.7 mg/mL) | 5 mcg |
| 8. | rhCC10 | 5 mcg |

Figure 7: HPLC analysis of mCPBA oxidation products

Figure 8: Isoelectric focusing of rhCC10 mCPBA reactions

1. Marker
2. blank
3. 2 eq mCPBA; 4°C
4. 5 eq mCPBA; 4°C
5. 10 eq mCPBA; 4°C
6. rhCC10
7. 2 eq mCPBA; 21°C
8. 5 eq mCPBA; 21°C
9. 10 eq mCPBA; 21°C Western blot of IEF gel of rhCC10 mCPBA reactions using anti-rhCC10 antibody 1. 2 eq mCPBA; 4°C
2. 5 eq mCPBA; 4°C
3. 10 eq mCPBA; 4°C
4. rhCC10
5. 2 eq mCPBA; 21°C
6. 5 eq mCPBA; 21°C
7. 10 eq mCPBA; 21°C Isoelectric focusing of rhCC10 mCPBA reactions;
additional conditions 1. IEF Marker
2. 2 eq mCPBA, with $CaCl_2$, 15 min
3. 100 eq mCPBA, 9 days
4. 100 eq mCPBA, 15 min
5. rhCC10

Purification & mass spectral analysis of mCPBA reaction
products: CC10 isoforms

Figure 12: Optimization of MPO-H$_2$O$_2$ reaction;
Effect of CaCl$_2$

Figure 13: HPLC analysis of MPO-$H_2O_2$ oxidation products

Isoelectric focusing analysis of MPO + $H_2O_2$ CC10 reactions

1. IEF Marker
2. rhCC10
3. 300ng MPO+50 eq $H_2O_2$; 1 hr
4. 600ng MPO+50 eq $H_2O_2$; 1 hr
5. 1000ng MPO+50 eq $H_2O_2$; 1 hr
6. 300ng MPO+50 eq $H_2O_2$; 24hr Western blot of IEF gels of rhCC10 MPO and $H_2O_2$ reactions using anti-rhCC10

1. IEF Marker
2. rhCC10
3. 300ng MPO+50 eq $H_2O_2$; 1 hr
4. 600ng MPO+50 eq $H_2O_2$; 1 hr
5. 1000ng MPO+50 eq $H_2O_2$; 1 hr
6. 300ng MPO+50 eq $H_2O_2$; 24hr Purification and mass spectral analysis of a CC10 isoform from a MPO-H$_2$O$_2$ reaction Figure 17: HPLC analysis of peroxynitrite oxidation products Figure 18: Effects of pH and CaCl$_2$ on peroxynitrite-mediated oxidation of rhCC10

Western blot analysis of peroxynitrite reaction products

Secretoglobin reaction products of ROS and RNS
detected with rhCC10 protein

Modification of rhCC10 by tissue transglutaminase

Figure 22

Enhanced anti-viral activity of modified CC10

Figure 23
Enhanced inhibition of neutrophil chemotaxis by modified CC10 ROS & RNS products
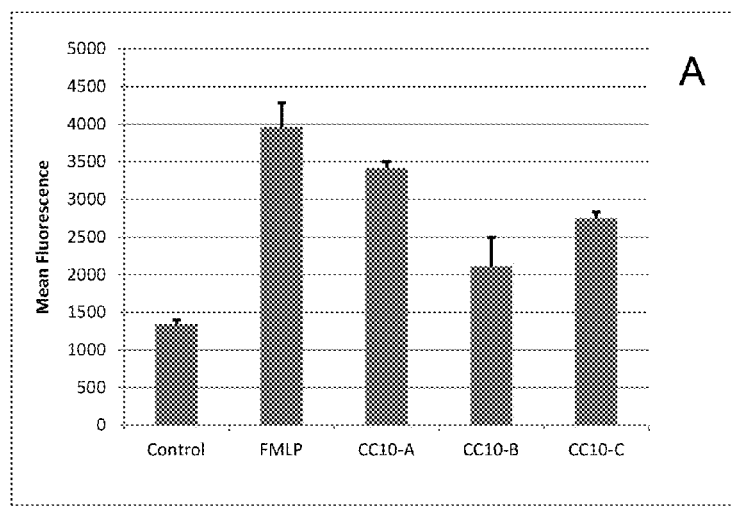
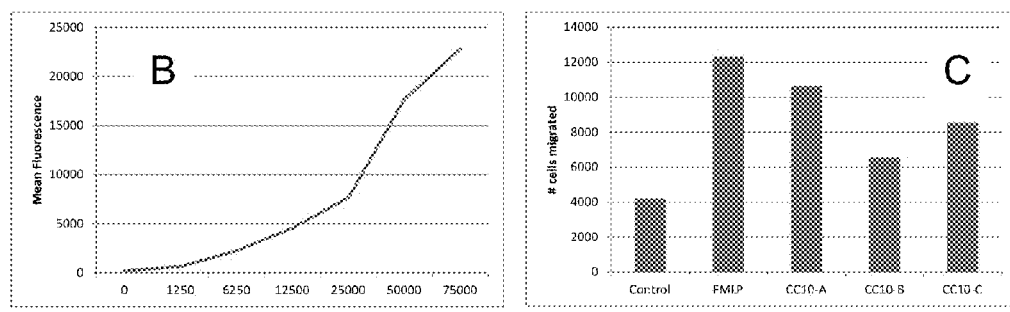

MODIFICATION AND COMPOSITIONS OF HUMAN SECRETOGLOBIN PROTEINS

FIELD OF THE INVENTION

The field of the invention pertains to chemically or enzymatically modified preparations of synthetic secretoglobins that have altered or enhanced properties compared to the unmodified versions. More specifically, modification of recombinant human secretoglobin proteins using reactive oxygen species (ROS), reactive nitrogen species (RNS), enzyme catalyzed modification such as myeloperoxidase plus hydrogen peroxide, or transglutaminase catalyzed modification. The invention further pertains to characterization of new isoforms of modified secretoglobins, optimized processes for modifying secretoglobins, and isolation of secretoglobin isoforms. The term "isoform" herein refers to a secretoglobin or CC10 monomer, dimer, or other multimer complex that contains intact monomers of at least 60 amino acids in length that contain one or more chemically modified amino acids. The invention further pertains to alteration of the biological activity, change in the structural conformation, or biochemical properties of a secretoglobin by chemical or enzymatic modification of one or more of its amino acids. The invention further pertains to enhancing the anti-viral activity of rhCC10 through chemical modification with ROS, RNS, and enzyme-catalyzed amino acid modification. The invention further pertains to enhancing the inhibition of neutrophil migration by rhCC10 through chemical modification with ROS, RNS, and enzyme-catalyzed amino acid modification.

BACKGROUND OF THE INVENTION

Secretoglobins are a family of structurally related proteins comprised of four helical bundle monomers that form disulfide dimers, tetramers and higher multimers. There are 8 known human secretoglobins (FIG. 1) and the Clara Cell 10 kDa protein (CC10), also known as uteroglobin, Clara Cell 16 kDa protein (CC16), Clara Cell secretory protein (CCSP), blastokinin, urine protein-1, and secretoglobin 1A1 (SCGB1A1), is the most abundant and well-known member of the family. Secretoglobins and CC10 are believed to exist in all vertebrate animals. Based on what is known of CC10, secretoglobins are thought to play a role in regulating immune responses, although the physiologic roles and specific mechanisms of these proteins, including CC10 remain unknown.

The primary source of CC10 in mammals is the pulmonary and tracheal epithelia, especially the non-ciliated bronchiolar airway epithelial cells (primarily Clara cells), and it is the most abundant locally-produced protein in the extracellular fluids of the adult lung. It is also secreted in the nasal epithelia. CC10 is also present in serum and urine, which is largely derived from pulmonary sources. CC10 is also produced by reproductive tissues (uterus, seminal vesicles), exocrine glands (prostate, mammary gland, pancreas), endocrine glands (thyroid, pituitary, adrenal, and ovary) and by the thymus and spleen (Mukherjee, 1999; Mukherjee, 2007). The major recoverable form of human CC10 in vivo is a homodimer, comprised of two identical 70 amino acid monomers, with an isoelectric point of 4.7-4.8. Its molecular weight is 15.8 kDa, although it migrates on SDS-PAGE at an apparent molecular weight of 10-12 kDa. In the native homodimer, the monomers are arranged in an antiparallel configuration, with the N-terminus of one adjacent to the C-terminus of the other and are connected by two disulfide bonds between Cys3 of one monomer and Cys69 of the other monomer (Mukherjee, 1999).

There are many chemical and enzymatic processes that modify amino acid residues on proteins. The secretoglobins undergo cleavage of N-terminal signal peptides, which is an integral part of the secretion process in mammalian cells. But they are not known to be glycosylated or lipidated. However, secretoglobins are subjected to the same processes that affect all other proteins in the extracellular milieu during an inflammatory response. Native CC10 is chemically modified in vivo and new forms of native CC10 have been identified in patient samples that are not present in samples from normal humans (Lindhal, 1999; Ramsay, 2001; Ariaz-Martinez, 2012). The modifications are presumed to be caused by inflammatory processes, since the new forms have only been identified in airway lining fluid (ALF) samples from patients with respiratory conditions characterized by ongoing or acute inflammation. Although some have speculated that the modifications to CC10 are the result of reactions with reactive oxygen species generated by the inflammatory response, the nature of the modifications is presently unknown. Furthermore, oxidative modification to native CC10 is thought to represent damage to the protein that impairs its anti-inflammatory activity and immunomodulatory function, thereby contributing to the development of chronic lung disease in premature infants who experience respiratory distress (Ramsay, 2001).

Synthetic CC10 protein may be made by recombinant or chemical synthetic methods (Barnes, 1996; Mantile, 1993; Nicolas, 2005). CC10 is the most well-known member of a family of structurally related proteins collectively called secretoglobins (Klug, 2000). The amino acid sequences for the mature secreted sequences of eight human secretoglobins are shown in FIG. 1. The N-termini are predictions based on consensus signal peptide cleavage sites and have not been confirmed by N-terminal sequencing of the native proteins. All secretoglobins share a conserved four helical bundle secondary structure and, therefore, generally believed to mediate similar physiological functions.

Reactive oxygen species (ROS) and reactive nitrogen species (RNS) are generated as a part of chronic inflammatory processes associated with aging and disease, or as a result of severe inflammatory responses to combat infections and other acute insults, such as smoke inhalation. Common ROS and RNS chemical reagents that mediate protein oxidation in vivo include hydrogen peroxide ($H_2O_2$), $Fe^{2+}$, $Cu^{1+}$, glutathione, HOCl, HOBr, $^1O_2$, and $ONOO^-$. ROS and RNS may be synthesized or released in vivo as a result of enzyme activity, such as myeloperoxidase, xanthine oxidase, and P-450 enzymes, and oxidative burst activity of activated phagocytic cells. Lipid peroxides such as 4-hydroxy-2-trans-nonenal (HNE), (MDA), and acrolein are the products of reactions of ROS and RNS with lipids that are, in turn, highly reactive and can form adducts with proteins. Ozone and UV light, as well as gamma irradiation in the presence of $O_2$ and mitochondrial electron transport chain leakage, also cause protein oxidation.

ROS and RNS are indiscriminate chemically reactive agents that destroy essential biological components including nucleic acids, lipids (including membrane and surfactant phospholipids), and proteins, in both the pathogen and host, often causing significant tissue damage that may be more life-threatening than the original infection or other cause of the inflammatory response. For example, acute respiratory distress syndrome (ARDS) is often triggered by an acute lung infection (pneumonia) that results in the release of ROS and RNS, and typically has a 40-60% mortality rate due to pulmonary tissue damage that compromises lung function, even after the pathogen causing the infection is brought under control using anti-microbial agents.

There are several types of oxidative protein modifications, the most common of which is sulfur oxidation in which disulfide bonds between cysteines (Cys), S-thiolation, and methionine (Met) sulfoxide are formed. Protein carbonyl groups are also common oxidative modifications in which amino acid side chains are converted to aldehydes and ketones, especially lysine (Lys) arginine (Arg), and proline (Pro). Aliphatic amino acids may be converted to their hydro (pero)xy derivatives. Chloramines and deaminations may occur. Certain amino acids may be converted into other amino acids, such as histidine (His) to asparagine (Asn), while others may form lipid peroxidation adducts, amino acid oxidation adducts (eg. p-hydroxyphenylacetaldehyde), and glycoxidation adducts (eg. carboxymethyllysine). At a macroscopic protein level, cross-links, aggregation, and peptide bond cleavage may occur as a result of exposure to ROS and RNS.

There 12 amino acids that are modified in vivo by ROS and RNS into several physiologic oxidation products, as shown in Table 1. In general, amino acids cysteine (Cys) and methionine (Met) are the most susceptible to oxidation and, unlike oxidation of other amino acids, the oxidation of Met and Cys are reversible (methionine sulfoxide reductase and glutathione and thioredoxin redox systems) (Stadtman, 2002).

Transglutaminases play a significant role in inflammation and immunity, particularly TG2 or tissue transglutaminase. It is present mostly in the cytoplasm but a portion of the enzyme is associated with the membrane on the cell surface and is known to be a coreceptor for fibronectin. TGs have also been shown to cross-link proteins to specific lipid moieties in membranes, allowing a lipid barrier to be created on a structural protein scaffold in skin (Lesort, 2000; Nemes, 1999). More recently, the emerging role of TGs in viral infection has been recognized (reviewed in Jeon, 2006). Intracellular TG2 is normally present in an inactive state and is activated by oxidative stress and calcium mobilization resulting from viral infection. Activated intracellular TG2 mediates its anti-viral activities via direct modification/inactivation of viral proteins, as well as modification of cellular proteins required for viral entry, replication, assembly, or transport. CC10 has been previously shown to be a substrate for TG2 (Mukherjee, 1988). CC10 is cross-linked to other CC10 molecules by TG2, to form covalently attached multimers and aggregates observed on SDS-PAGE gels and Western blots. However, no other TG-mediated reaction products of CC10 or other secretoglobin have been characterized.

TABLE 1

Amino acid modifications caused by ROS and RNS

| Amino Acid | Physiological oxidation products | Number per CC10 monomer |
|---|---|---|
| Cysteine (Cys) | Disulfides, glutathiolation, HNE-Cys | 2 |
| Methionine (Met) | Methionine sulfoxide | 4 |
| Tyrosine (Tyr) | Dityrosine, nitrotyrosine, chlorotyrosines, dopa | 1 |
| Phenylalanine (Phe) | Tyrosine (hydroxyphenylalanine) | 2 |
| Valine (Val) & Leucine (Leu) | Peroxides (hydroxides) | 9 |
| Glutamate (Glu) | Oxalic acid, pyruvic acid | 6 |
| Proline (Pro) | Hydroxyproline, pyrrolidone, glutamic semialdehyde | 4 |
| Threonine (Thr) | 2-amino-3-ketobutyric acid | 3 |
| Arginine (Arg) | Glutamic semialdehyde, chloramines | 3 |
| Lysine (Lys) | a-aminoadipic semialdehyde, chloramines, MDA-Lys, HNE-Lys, acrolein-Lys, carboxymethyllysine, pHA-Lys | 5 |
| Tryptophan (Trp) | Hydroxytryptophan, Nitro-tryptophan, kynurenines | 0 |
| Histidine (His) | 2-oxohistidine, asparagine, aspartate, HNE-His | 0 |

Modification of secretoglobins may also be mediated enzymatically, not just by the downstream effects of ROS and RNS generated by enzymes such as MPO, but also by transglutaminase enzymes (TGs). TGs are ubiquitous in nature, found in all forms of life from microbes to mammals. TGs are essential to several inter- and intracellular processes in mammals, including extracellular matrix synthesis, neutrophil and monocyte adhesion and motility, receptor endocytosis, pinocytosis, antigen uptake and processing, blood clotting, G-protein signaling, and apoptosis (reviewed in Lorand, 2003). TGs are multi-functional enzymes that mediate at least one main enzymatic activity; the classical transglutaminase activity in which a glutamine residue in one protein serves as an acyl donor and a lysine residue in a second protein serves as the acyl acceptor. TGs also mediate deamidation and esterification of proteins, as well as the creation and rearrangement of disulfide bonds between cysteine residues. None of these activities has an energy requirement and the only cofactor necessary is calcium.

OBJECTS OF THE INVENTION

The foregoing provides a non-exclusive list of the objectives achieved by the present invention:

A primary object of the invention is a composition of matter comprised of an oxidatively or enzymatically modified synthetic secretoglobin (whether made by recombinant or chemical methods).

A further object of the invention is a composition of matter comprised of an oxidatively or enzymatically modified synthetic CC10 (whether made by recombinant or chemical methods).

A further object of the invention is a composition of matter comprised of an oxidatively or enzymatically modified synthetic SCGB3A2 (whether made by recombinant or chemical methods).

A further object of the invention is a composition of matter comprised of an oxidatively or enzymatically modified synthetic SCGB3A1 (whether made by recombinant or chemical methods).

A further object of the invention is a composition of matter comprised of an oxidatively or enzymatically modified synthetic SCGB2A1 (whether made by recombinant or chemical methods).

A further object of the invention is a composition of matter comprised of an oxidatively or enzymatically modified synthetic SCGB2A2 (whether made by recombinant or chemical methods).

A further object of the invention is a composition of matter comprised of an oxidatively or enzymatically modified synthetic SCGB1D1 (whether made by recombinant or chemical methods).

A further object of the invention is a composition of matter comprised of an oxidatively or enzymatically modified synthetic SCGB1D2 (whether made by recombinant or chemical methods).

A further object of the invention is a composition of matter comprised of an oxidatively or enzymatically modified synthetic SCGB1D4 (whether made by recombinant or chemical methods).

A further object of the invention is a composition of matter comprised of a modified synthetic secretoglobin containing one or more methionine sulfoxides.

A further object of the invention is a composition of matter comprised of a modified synthetic secretoglobin containing one or more cysteine glutathiolates.

A further object of the invention is a composition of matter comprised of a modified synthetic secretoglobin containing one or more HNE-cysteines.

A further object of the invention is a composition of matter comprised of a modified synthetic secretoglobin containing one or more nitrotyrosines.

A further object of the invention is a composition of matter comprised of a modified synthetic secretoglobin containing one or more di-tyrosines.

A further object of the invention is a composition of matter comprised of a modified synthetic secretoglobin containing one or more carbonyl groups.

A further object of the invention is a composition of matter comprised of a modified synthetic secretoglobin containing a combination of two or more modified amino acids selected from the groups consisting of methionine sulfoxide, nitrotyrosine, or di-tyrosine.

A further object of the invention is a composition of matter comprised of a modified synthetic secretoglobin containing one or more chlorotyrosines.

A further object of the invention is a composition of matter comprised of a modified synthetic secretoglobin containing one or more hydroxyprolines, pyrrolidones, or glutamic semialdehydes.

A further object of the invention is a composition of matter comprised of a modified synthetic secretoglobin containing one or more 2-amino-3-ketobutyric acids.

A further object of the invention is a composition of matter comprised of a modified synthetic secretoglobin containing one or more chloramines.

A further object of the invention is a composition of matter comprised of a modified synthetic secretoglobin containing one or more α-aminoadipic semialdehyde, chloramines, MDA-Lys, HNE-Lys, acrolein-Lys, carboxymethyllysine, or pHA-Lys.

A further object of the invention is a composition of matter comprised of a modified synthetic secretoglobin containing one or more hydroxytryptophan, nitro-tryptophan, or kynurenines.

A further object of the invention is a composition of matter comprised of a modified synthetic secretoglobin containing one or more valine or leucine peroxides.

A further object of the invention is a composition of matter comprised of a modified synthetic secretoglobin containing one or more oxalic or pyruvic acids.

A further object of the invention is a composition of matter comprised of a modified synthetic secretoglobin containing one or more hydroxyphenylalanines.

A further object of the invention is a composition of matter comprised of a modified synthetic secretoglobin containing one or more glutamic semialdehydes.

A further object of the invention is a composition of matter comprised of a modified synthetic secretoglobin containing one or more 2-oxohistidine or HNE-His.

A further object of the invention is a composition of matter containing a combination of an unmodified synthetic secretoglobin and an oxidatively or enzymatically modified synthetic secretoglobin, wherein the unmodified and modified preparations are the same secretoglobin.

A further object of the invention is a composition of matter containing a combination of an unmodified synthetic secretoglobin and an oxidatively or enzymatically modified synthetic secretoglobin, wherein the unmodified and modified preparations are not the same secretoglobin.

A further object of the invention is a composition of matter containing a combination two or more oxidatively or enzymatically modified synthetic secretoglobins, wherein the unmodified and modified preparations are the same secretoglobin.

A further object of the invention is a composition of matter containing a combination two or more oxidatively or enzymatically modified synthetic secretoglobins, wherein the unmodified and modified preparations are not the same secretoglobin.

A further object of the invention is a composition of matter containing a combination one or more unmodified synthetic secretoglobin and one or more oxidatively or enzymatically modified synthetic secretoglobins, wherein the unmodified and modified preparations are the same secretoglobin.

A further object of the invention is a composition of matter containing a combination one or more unmodified synthetic secretoglobin and one or more oxidatively or enzymatically modified synthetic secretoglobins, wherein the unmodified and modified preparations are not the same secretoglobin.

A secondary object of the invention is a pharmaceutical composition containing a modified synthetic secretoglobin that can be used as a therapeutic agent.

A further object of the invention is a pharmaceutical composition containing a combination of two or more modified synthetic secretoglobins that can be used as a therapeutic agent.

A further object of the invention is a pharmaceutical composition containing a combination of unmodified and modified synthetic secretoglobins that can be used as a therapeutic agent.

It is a further object of the invention to administer a modified synthetic secretoglobin to a patient with an inflammatory condition or a viral infection.

It is a further object of the invention to administer a modified synthetic secretoglobin to a patient with a respiratory disease or condition, an autoimmune disease or condition, a fibrotic condition, a metabolic disease, an infectious disease, or any acute or chronic inflammatory condition or disease.

It is a further object of the invention to administer a modified synthetic secretoglobin to a patient any condition characterized by a deficiency of the native secretoglobin isoform corresponding to the modified synthetic secretoglobin to be administered.

It is a further object of the invention to administer a modified synthetic secretoglobin to treat or prevent a severe exacerbation of an underlying condition in a patient with an underlying chronic disease or condition.

It is a further object of the invention to administer a modified synthetic CC10 to a patient with an inflammatory condition or a viral infection.

It is a further object of the invention to administer a modified synthetic CC10 to a patient with a respiratory disease or condition, an autoimmune disease or condition, a fibrotic condition, a metabolic disease, an infectious disease, or any acute or chronic inflammatory condition or disease.

It is a further object of the invention to administer a modified synthetic CC10 to a patient any condition characterized by a deficiency of the native CC10 isoform corresponding to the modified synthetic CC10 to be administered.

It is a further object of the invention to administer a modified synthetic CC10 to treat or prevent a severe exacerbation of an underlying condition in a patient with an underlying chronic disease or condition.

It is another object of the invention to use a modified synthetic secretoglobin that can be used to develop a diagnostic assay to evaluate patient samples.

It is further object of the invention to use a modified synthetic secretoglobin as a standard that can be used in a diagnostic assay to evaluate patient samples.

It is further object of the invention to use a modified synthetic CC10 that can be used to develop a diagnostic assay to evaluate patient samples.

It is a further object of the invention to use a modified synthetic CC10 in a standard that can be used in a diagnostic assay to evaluate patient samples.

It is a further object of the invention to use a modified synthetic secretoglobin as a standard to enable the purification of a modified native secretoglobin from a biological source such as blood, urine, or tissue.

It is a further object of the invention to use a modified synthetic secretoglobin as a standard to enable the development of a process to purify of a modified native secretoglobin from a biological source such as blood, urine, or tissue.

It is a further object of the invention to use a modified synthetic secretoglobin as a standard to monitor a process to purify of a modified native secretoglobin from a biological source such as blood, urine, or tissue.

It is a further object of the invention to use a modified synthetic secretoglobin as a standard to control the quality of a modified native secretoglobin purified from a biological source such as blood, urine, or tissue.

A further object of the invention is a process in which chemical oxidation is used to convert an unmodified synthetic secretoglobin into a modified synthetic secretoglobin.

A further object of the invention is a process in which a reactive oxygen species (ROS) is used to convert an unmodified synthetic secretoglobin into a modified synthetic secretoglobin.

A further object of the invention is a process in which a reactive nitrogen species (RNS) is used to convert an unmodified synthetic secretoglobin into a modified synthetic secretoglobin.

A further object of the invention is a process in which sodium hypochlorite (NaOCl) is used to convert an unmodified synthetic secretoglobin into a modified synthetic secretoglobin.

A further object of the invention is a process in which hypochlorite (HOCl) is used to convert an unmodified synthetic secretoglobin into a modified synthetic secretoglobin.

A further object of the invention is a process in which metachloroperbenzoic acid (mCPBA) is used to convert an unmodified synthetic secretoglobin into a modified synthetic secretoglobin.

A further object of the invention is a process in which hydrogen peroxide ($H_2O_2$) is used to convert an unmodified synthetic secretoglobin into a modified synthetic secretoglobin.

A further object of the invention is a process in which an enzyme is used to convert an unmodified synthetic secretoglobin into a modified synthetic secretoglobin.

A further object of the invention is a process in which myeloperoxidase is used to convert an unmodified synthetic secretoglobin into a modified synthetic secretoglobin.

A further object of the invention is a process in which transglutaminase is used to convert an unmodified synthetic secretoglobin into a modified synthetic secretoglobin.

A further object of the invention is a process in which transglutaminase is used to attach a label, chemical, lipid, or peptide moiety to an unmodified synthetic secretoglobin.

BRIEF DESCRIPTION OF THE DRAWINGS

FIG. 1: Amino acid sequences of secretoglobins. The amino acid sequences of the monomer forms of eight human secretoglobins are shown. All sequences were taken from Genebank and signal peptides of the translation products have been removed to show the predicted N-termini of each monomer. All secretoglobins share a conserved four helical bundle secondary structure and form homodimers, heterodimers, tetramers, and large multimers.

FIG. 2: HPLC pattern of rhCC10 reacted with NaOCl. Preparations of unmodified rhCC10 and rhCC10 reacted with increasing amounts of NaOCl oxidant equivalents were analyzed by reverse phase HPLC using a C-18 column. The arrow points to the unmodified rhCC10 peak in reaction mixtures. Approximately 25 mcg of protein was loaded for each HPLC run shown.

FIG. 22: Enhanced inhibition of viral replication by modified rhCC10. Neutral red assay indicating cell survival with and without infection by two strains of influenza and in the presence of 1 mg/ml unmodified and modified rhCC10.

FIG. 23: Enhanced inhibition of neutrophil chemotaxis by modified rhCC10. Fluorescence measurements of migrated differentiated PLB-985 cells differentiated in the presence of 100 mcg/ml of unmodified rhCC10 (CC10-A), NaOCl-modified rhCC10 (CC10-B), and mCBPA-modified rhCC10 (CC10-C).

SUMMARY OF THE INVENTION

The invention relates to chemical and/or enzymatic modification of synthetic secretoglobins in order to alter or enhance biological or biochemical properties compared to the unmodified versions. Chemical reagents such as reactive oxygen species (ROS), and reactive nitrogen species (RNS), or enzymes such as myeloperoxidase or transglutaminase, are used to achieve the amino acid modifications. The addition of lipid and other moieties to secretoglobins is also mediated by TGs. The invention further relates to optimization of chemical or enzyme-mediated processes to achieve amino acid modifications, as well as biochemical and physical characterization of mixtures of modified secretoglobins, and isolation and characterization of individual secretoglobin isoforms. The term "isoform" herein refers to a secretoglobin monomer, dimer, or other multimer complex that contains monomer units of at least 60 amino acids in length, but preferably full length monomers that are at least 75% identical to the amino acid sequences shown in FIG. 1, that contain one or more chemically modified amino acids. Biological properties including, but not limited to, inhibition of viral replication and inhibition of neutrophil chemotaxis may be altered or enhanced in the chemically modified secretoglobin mixtures and isoforms.

DETAILED DESCRIPTION

The modification of secretoglobins by ROS, RNS, and enzymatic activity such as MPO and TG2 has not been investigated in detail. Preliminary reports suggest that native CC10 is modified during acute inflammatory responses in vivo, such as in respiratory distress, giving rise to new isoforms thus far identified by cross-reactivity with anti-CC10 antibodies and isoelectric points different from unmodified CC10 (pl ~4.8), which is the predominant form in biological fluid samples. It has also been reported that CC10 is a substrate for tissue transglutaminase in vitro. Other than the role for Cys residues in stabilizing multimers and controlling access to the central hydrophobic cavity, there is no known physiological role for oxidation of any amino acid in any secretoglobin. We believe that reversible oxidation of Cys and Met residues is a protective physiologic mechanism by which CC10 and other secretoglobins are able to scavenge harmful ROS from the local environment, thereby sparing tissue during an inflammatory response. We further believe that the oxidation status of Cys and Met residues in secretoglobins affects the biochemical and biological properties but does not represent protein damage that results in loss of function, rather the properties and function of the oxidized secretoglobins are modulated. Likewise, oxidative and/or enzymatic modification of other secretoglobin amino acids such as tyrosine, lysine, glutamine, valine, leucine, phenylalanine, glutamate, arginine, threonine, proline, histidine, and tryptophan do not represent protein damage, but rather modulate biochemical and biological properties that enable different or enhanced activities.

The majority of known, specific ROS, RNS, and MPO-mediated amino acid modifications are associated with protein damage and loss of function. Accumulation of oxidized protein is associated with disease and aging processes (Berlett and Stadtman, 1997) However, recognition of reversible oxidation is emerging as a regulatory mechanism for modifying protein function and not just a form of damage that inactivates proteins. All eight human secretoglobins contain Cys residues that are believed to typically exist in a naturally oxidized state in which disulfide bonds between conserved cysteines at the N- and C-termini stabilize homo- and heterodimers, tetramers, and higher multimers. All cysteines in secretoglobins are potentially susceptible to oxidation and the formation of intra- or intermolecular disulfide bonds, particularly the respiratory secretoglobins, CC10, SCGB3A1, and SCGB3A2. The disulfide bonds between N- and C-terminal Cys in CC10 certainly stabilize the homodimer in conditions that would otherwise break apart the dimer into monomers, such as in non-reducing SDS-PAGE conditions. Similarly, the internal Cys of SCGB3A2 (Cys60 of the sequence shown in FIG. 1) stabilizes the homodimer in vitro. No particular functionality is ascribed to the dimer versus the monomer or other multimers of CC10 or SCGB3A2. However, since CC10 and SCGB3A2 both form homodimers spontaneously in vitro without any requirement for an oxidizing agent, it has not been possible to evaluate differences in biochemical properties or biological activities of forms other than the dimer. These homodimers are very stable in vitro, although there is an equilibium between monomer and dimer in any given aqueous environment and it is possible to change buffer conditions to favor a higher percentage of monomer and/or tetramer with respect to dimer. Despite that the dimer is the initial form administered to humans and animals, numerous reducible and non-reducible forms can be recovered from biological fluids (Antico, 2006). Physiologically, the in vivo glutathione redox system in the lungs likely mediates reversible oxidation of disulfide bonds in the respiratory secretoglobins and other secretoglobins that may be found in the lungs.

A physiological role for CC10 has been proposed to be the scavenging of toxic or otherwise harmful hydrophobic moieties that may be taken up and bound into the central hydrophobic cavity and thereby removed from the local tissue environment (Peter, 1992; Hard, 1995; Umland, 1992; 1994). The disulfide bonds between the Cys residues (Cys3 and Cys69) of the monomer components in each CC10 dimer are believed to act like a gate that opens and closes by reversible oxidation of the Cys residues to form and break the disulfide bonds to allow entry of a hydrophobic moiety into the central hydrophobic cavity, then trap it there. Several studies have reported the strong binding of putative in vivo CC10 ligands such as a polychlorinated biphenyls and progesterone, inside the dimer and that specific residues such as Phe6 and Tyr21 stabilize ligand binding (Callebaut, 2000).

All secretoglobins contain significant proportions of amino acids that are susceptible to oxidative and enzymatic amino acid modification. Each 70 amino acid monomer of CC10 contains a total of 42 amino acids (out of 70; >50%), listed in Table 1, that can be oxidized by physiologic processes involving ROS and RNS, leaving open the possibility of a large number of ROS and RNS reaction products, aka isoforms. TG can also be used to attach lipid or other moieties to secretoglobins via their glutamine, lysine, and cysteine residues, and not just cross-link secretoglobins to other proteins. As illustrated in the following examples, we have herein found this to be the case with rhCC10, in which oxidative and enzymatic modifications give rise to multiple isoforms that can be isolated and characterized. Preparations containing oxidatively modified rhCC10 also mediated enhanced of inhibition of viral replication and neutrophil chemotaxis, representing significant improvements on the existing unmodified CC10 drug preparation. Furthermore, the use of rhCC10 preparations modified in vitro as standards to assess CC10 isoforms contained within, or isolated from, biological samples, enables the evaluation of native CC10 isoforms as biomarkers of pulmonary status in chronic diseases and acute conditions. Thus, in the absence of oxidative or enzymatic amino acid modification, a secretoglobin may have no effect on a particular cell type, but has a different effect after modification because the modification enabled or disabled binding to a cell surface receptor, cell signaling molecule, lipid, ligand, structural protein, or other intra- or extracellular component. The effects of oxidative and/or enzymatic amino acid modification on the biochemical and biological properties of secretoglobins, therefore, opens up new possibilities for the use of modified secretoglobins in mediating pharmacological effects not previously possible using unmodified preparations, as well as for use as standards to evaluate novel isoforms of native secretoglobins as biomarkers of disease status in various patients, including, but not limited to patients with cancer, respiratory diseases, autoimmune diseases, acute or chronic infections, allergies, metabolic diseases, cardiovascular diseases, hematologic disorders, and exposures to smoke, chemical pollutants, toxins or other insult.

EXAMPLES

Example 1

Chemical Modification of rhCC10 by ROS: Sodium Hypochlorite (NaOCl)

Each reaction was initiated at ~4° C. (on ice) by adding NaOCl (9.2 µL; 0.05% solution in water, 62.1 nmol, 5 equivalents) to a solution of the protein (0.2 mg, 12.42 nmol) in 10 mM phosphate buffer, pH 7.4 or plain water, mixing briefly and incubating on ice for 15 minutes in the dark (total volume of 0.2 mL). The reaction was quenched by adding L-methionine (9.3 µL; 10 mM in water, 93.15 nmol), then incubated for 20 min and warmed to room temperature.

Several reactions were performed using equivalents of the oxidant ("oxidant equivalents") ranging from 1-100. Oxidation of rhCC10 was monitored using HPLC, in which new modified isoforms appeared as new HPLC peaks, eluting earlier than unmodified rhCC10, as shown in FIG. 2. Reactions were concentrated by Speedvac and then resuspended in water. Approximately 25 µg of each sample was injected onto the HPLC column (VYDAC Polymeric C18 column 300 Å 5 µm, 2.1 mm×250 mm, Cat #218TP52) on an Agilent 1100 system using a mobile phase as follows: A: water; B: 95% acetonitrile+5% water (both containing 0.1% TFA) at a flow rate of 0.3 mL/min. Output was monitored by UV absorption at 214 nm.

Figure 3:
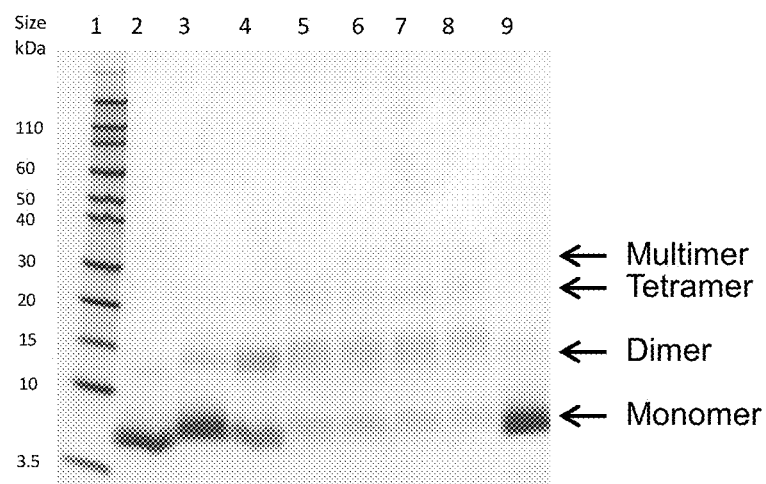
FIG. 3: SDS-PAGE of rhCC10 NaOCl reactions. A 10-20% tricine SDS-PAGE gel was used. Preparations of rhCC10 modified with increasing amounts of NaOCl; numbers of oxidant equivalents are shown for each lane. All samples, each containing ~5 mcg protein, were reduced with 1 mM DTT in SDS loading buffer and heated to 65° C. for 15 minutes prior to gel loading.

Increasing the number of oxidant equivalents of NaOCl increased the number of rhCC10 isoforms as well as the peak heights, indicating increased amounts of each isoform as the reaction progressed. At 20 oxidant equivalents, the HPLC shows that essentially all of the unmodified rhCC10 is gone and only modified isoforms remain. SDS-PAGE of these preparations under reducing conditions showed monomeric protein (6 kDa) as expected, but also showed dimer (~12 kDa), tetramer (~24 kDa), hexamer (~32 kDa), and higher multimer bands remaining, as shown in FIG. 3. This is the first report of a tetramer formed by CC10 and stable to reducing SDS-PAGE conditions in the absence of transglutaminase activity. The presence and predominance of the monomer indicates that the amino acid sequence for rhCC10 is largely intact. Even at 100 oxidant equivalents, there are faint CC10 monomer, dimer, tetramer, and higher multimer bands on SDS-PAGE, although the majority of protein is missing and appears to be destroyed with that many oxidation equivalents.

Figure 4:
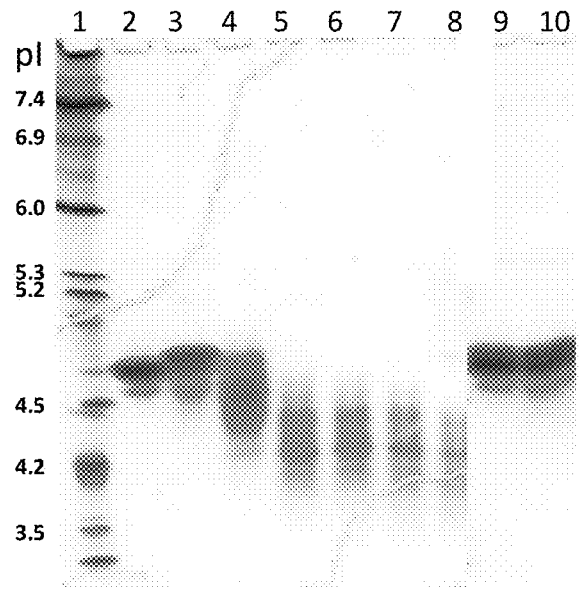
FIG. 4: Isoelectric focusing (IEF) of rhCC10 NaOCl reactions. The IEF gel covered pH range from 3-7. Preparations of rhCC10 modified with increasing amounts of NaOCl; numbers of oxidant equivalents are shown for each lane. All samples contain ~25 mcg protein. Samples were not reduced, exposed to SDS, or heated prior to gel loading.
Figure 5:
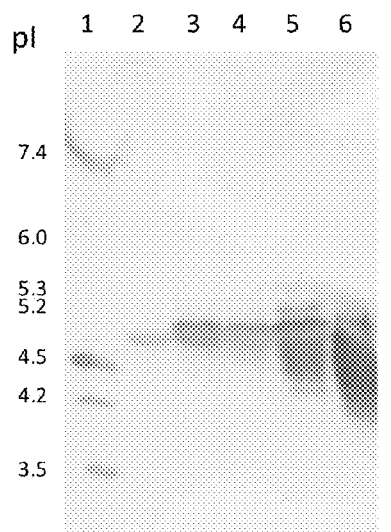
FIG. 5: Western blot of IEF gel of rhCC10 NaOCl reactions using anti-rhCC10 antibody. The IEF gel covered pH range from 3-7 and was blotted to PVDF membrane, then probed with a Protein-A purified rabbit polyclonal antibody prepared using unmodified rhCC10 as the antigen. Preparations of rhCC10 modified with NaOCl reaction conditions shown in lane descriptions. All samples contain ~25 mcg protein. Samples were not reduced, exposed to SDS, or heated prior to gel loading.

Interactions of the modified and unmodified rhCC10 with the C-18 column reflect hydrophobic interactions between the protein and chromatography resin. The modified isoforms elute faster than the unmodified rhCC10, indicating that the amino acid residues on the surface of the modified protein are less hydrophobic than the unmodified protein. Changes in the surface hydrophobicity pattern likely correspond with changes in surface charge, which can be measured by the isoelectric point. Samples were analyzed by isoelectric focusing using pH 3-7 isoelectric focusing gels as shown in FIG. 4. There is a progressive shift in pI towards more acidic isoforms less than 4.5. There is also a band at pI~5.5 in the reactions with 2 and 5 equivalents that disappears at 20 equivalents and may represent a reaction intermediate. Analysis of these reactions by Western blot of the IEF gel shows that all acidic NaOCl isoforms <4.5 are recognized by a rabbit polyclonal anti-rhCC10 antibody as shown in FIG. 5, however, the tetramer is not recognized by the polyclonal anti-rhCC10 antibody.

Figure 6:
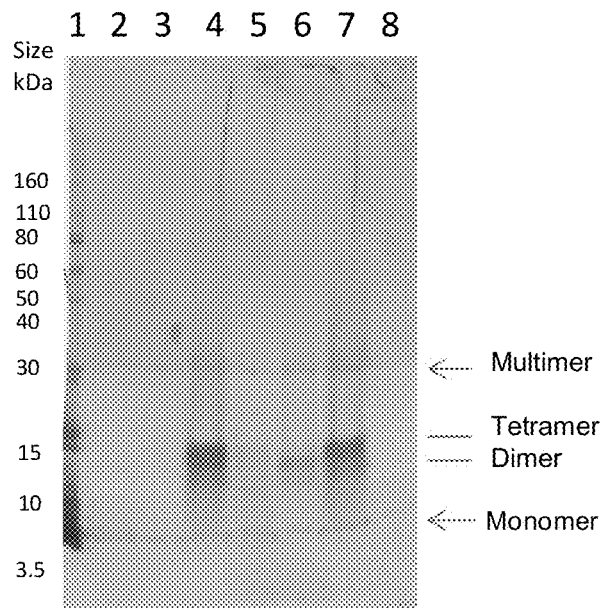
FIG. 6: Western blot of DNPH-treated rhCC10 NaOCl reactions using anti-DNP antibody. A 10-20% tricine SDS-PAGE gel was run on the modified rhCC10 preparations. NaOCl reaction products were run alongside MPO and mCPBA reaction products. The gel was blotted to PVDF then probed with rabbit polyclonal anti-DNP antibody (commercially available). Samples were not reduced but were mixed with SDS PAGE loading buffer and heated to 65° C. for 15 minutes prior to loading. Unmodified rhCC10 and MPO and mCPBA reaction products were not recognized by the antibody under the conditions used. Only the NaOCl reaction products contained detectable DNP, indicating the presence of carbonyl groups in these preparations.

The extent of the chemical reaction and modification of rhCC10 can be estimated by the detection of reactive carbonyl groups. The presence of carbonyl groups in ROS-reacted rhCC10 samples can be detected by labeling the carbonyl groups with 2,4-dinitrophenylhydrazine (DNPH), which adds a dinitrophenylhydrazone group (DNP), then analyzing the reaction products by Western blot using anti-DNP antibody as shown in FIG. 6. There is a baseline signal for monomer and tetramer in the unmodified CC10 (lane 8), which is exceeded in all other samples, regardless of type of ROS used in the reaction. Therefore, all ROS reactions produced some species that contained carbonyl groups. The unmodified dimer, and dimer in MPO and mCPBA modified preps show no reactivity and even blocked the background (see "ghost bands" at dimer position in lanes 2, 3, and 8.) There appears to be a combination effect of rhCC10 concentration and buffer in the NaOCl reaction. The signal strength in lane 4 is over 10× greater than lane 5, which is more than expected by the 2× difference in protein present. This suggests that higher rhCC10 concentration provides for a more extensive reaction than lower concentration when the reaction is done in water. The signal strength in lanes 4 and 7 is equal, despite that lane 7 contains half the protein, indicating that the reaction is more efficient in 10 mM phosphate buffer, pH 7.4 than in water. The signal strength in lane 6 is much less than in lane 7, despite that the same amount of protein is present. These observations indicate that the NaOCl reaction was more efficient when rhCC10 concentration is lower in the presence of buffer. Therefore, effect of rhCC10 concentration on reaction efficiency is opposite in water versus buffer. These differences illustrate how the process for chemical modification of rhCC10 with NaOCl is optimized. For example, an optimized process for NaOCl-mediated chemical modification of CC10 would involve the use of a lower concentration of rhCC10, in the presence of a low strength phosphate buffer at neutral pH.

Example 2

Chemical Modification of rhCC10 by ROS: mCPBA

Each reaction was initiated at ~24° C. (room temperature) by adding meta-choloroperbenzoic acid (mCPBA) (6.21 µL, 2 mM in water, 12.42 nmol, 2 equivalents) in 1 portion to a solution of the protein (0.1 mg, 6.21 nmol) in water at 24° C. and incubating for 15 minutes in the dark with occasional stirring (total volume of 0.2 mL). The reaction was stopped by the addition of L-methionine (1.8 µL; 10 mM in water, 18.6 nmol) and incubated for 20 min at 24° C. Several reactions were performed using oxidant equivalents of mCPBA ranging from 2-100.

Figure 7:
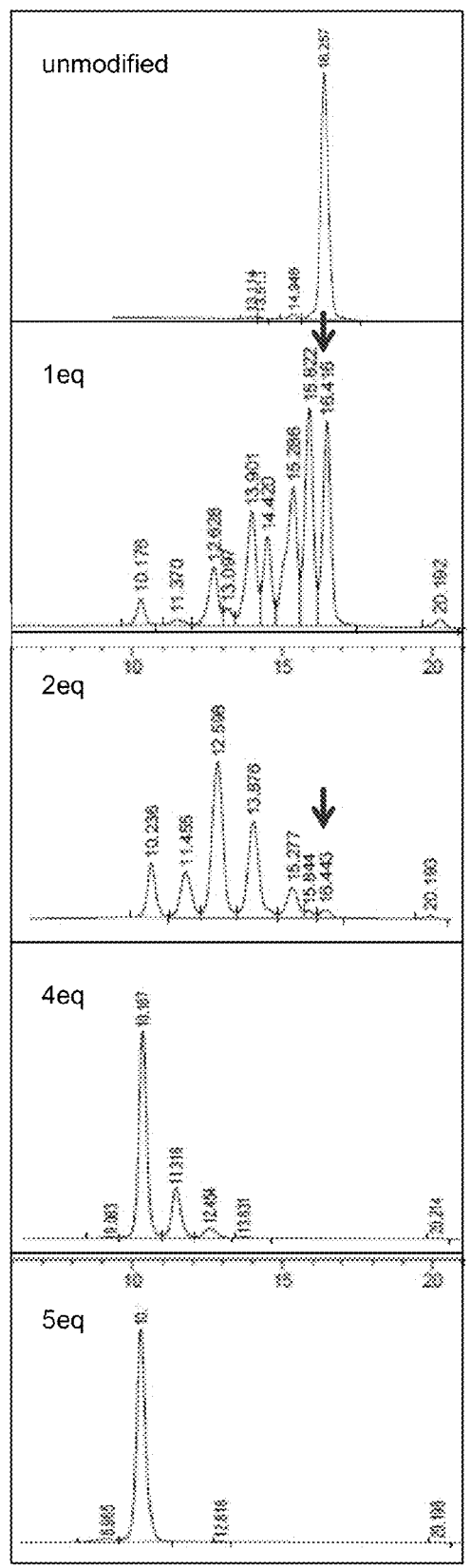
FIG. 7: HPLC analysis of mCPBA oxidation products. Preparations of unmodified rhCC10 and rhCC10 reacted with increasing amounts of mCPBA oxidant equivalents were analyzed by reverse phase HPLC using a C-18 column. The arrow points to the unmodified rhCC10 peak in reaction mixtures. Approximately 25 mcg of protein in each sample was loaded for each HPLC run shown.
Figure 8:
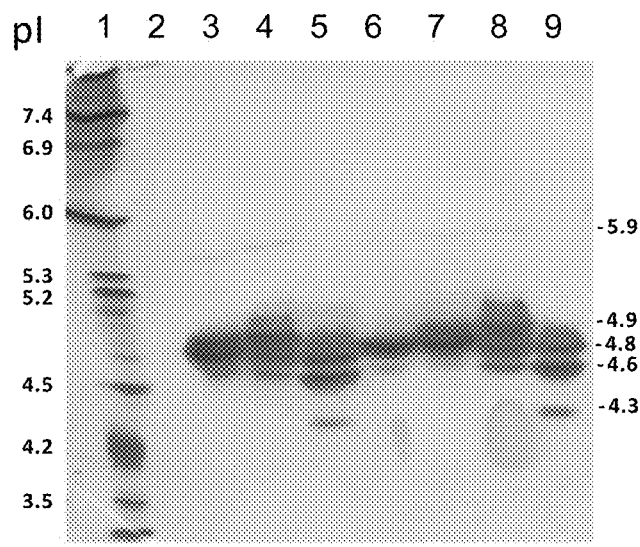
FIG. 8: Isoelectric focusing of rhCC10 mCPBA reactions. The IEF gel covered pH range from 3-7. Preparations of rhCC10 modified with increasing amounts of mCPBA; numbers of oxidant equivalents are shown for each lane and two different temperatures were tested. All samples contain ~25 mcg protein. Samples were not reduced, exposed to SDS, or heated prior to gel loading.
Figure 9:
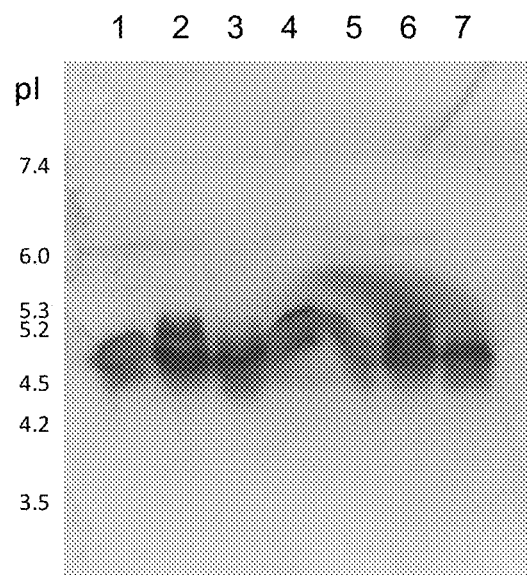
FIG. 9: Western blot of IEF gel of rhCC10 mCPBA reactions using anti-rhCC10 antibody. The IEF gel covered pH range from 3-7 and was blotted to PVDF membrane, then probed with Protein-A purified rabbit polyclonal antibody raised against rhCC10. Preparations of rhCC10 modified with increasing amounts of mCPBA; numbers of oxidant equivalents are shown for each lane and two different temperatures were tested. All samples contain ~25 mcg protein. Samples were not reduced, exposed to SDS, or heated prior to gel loading.
Figure 10:
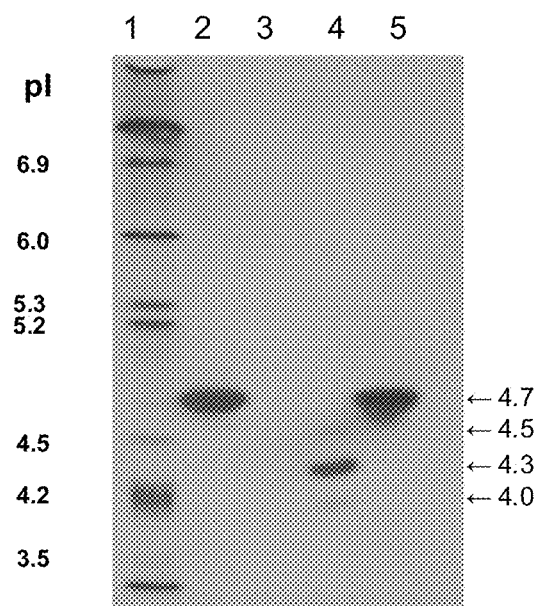
FIG. 10: Isoelectric focusing of rhCC10 mCPBA reactions; additional conditions. The IEF gel covered pH range from 3-7. Preparations of rhCC10 modified with mCPBA under additional conditions, including the presence of $CaCl_2$ and comparison of much higher numbers of oxidant equivalents. All samples contain ~25 mcg protein. Samples were not reduced, exposed to SDS, or heated prior to gel loading.

Oxidation of rhCC10 was monitored using HPLC. Reactions were concentrated in a Speedvac and then resuspended in water. Approximately 25 µg of each sample was injected onto the HPLC, as with the NaOCl reactions. New modified isoforms appeared as new HPLC peaks, eluting earlier than unmodified rhCC10, as shown in FIG. 7. Isoelectric focusing of the mCPBA reactions, shown in FIG. 8, revealed that multiple new isoforms were generated, including a cluster of new isoforms in the pI 4.5-5.2 range (4.6, 4.7, 4.9, 5.1, 5.2), two isoforms above 5.3 (~5.5, ~5.8) and one isoform below 4.5 (~4.3). These additional 8 bands differed from the original unmodified rhCC10 with a major band at pI 4.8 and a minor band at ~4.65. An important parameter in optimization of the reaction is temperature. The temperature of the reaction, 4° C. vs 21° C., did not affect the products or the apparent proportions of each product. Western blot of the IEF gel, shown in FIG. 9, demonstrated that the majority of these isoforms are recognized by a rabbit polyclonal antibody raised against rhCC10. However, like the tetramer form generated by the NaOCl reaction, the band at pI 4.3 was not recognized by the anti-rhCC10 antibody, suggesting that the structure of the protein was dramatically changed when 10 eq mCPBA were used. The isoforms below the main immunoreactive band at 4.8, also showed less signal than would be expected based on the intensity of staining in the IEF gel. Further analysis of reaction conditions showed that the presence of $CaCl_2$ could prevent modification of rhCC10 by mCPBA (FIG. 10, lane 2), that 100 eq mCPBA completely eliminates all of the original unmodified protein leaving only more acidic isoforms (pIs 4.0, 4.3, 4.5; lane 4), and that rhCC10 is destroyed if the reaction is run too long (lane 3).

Figure 11:
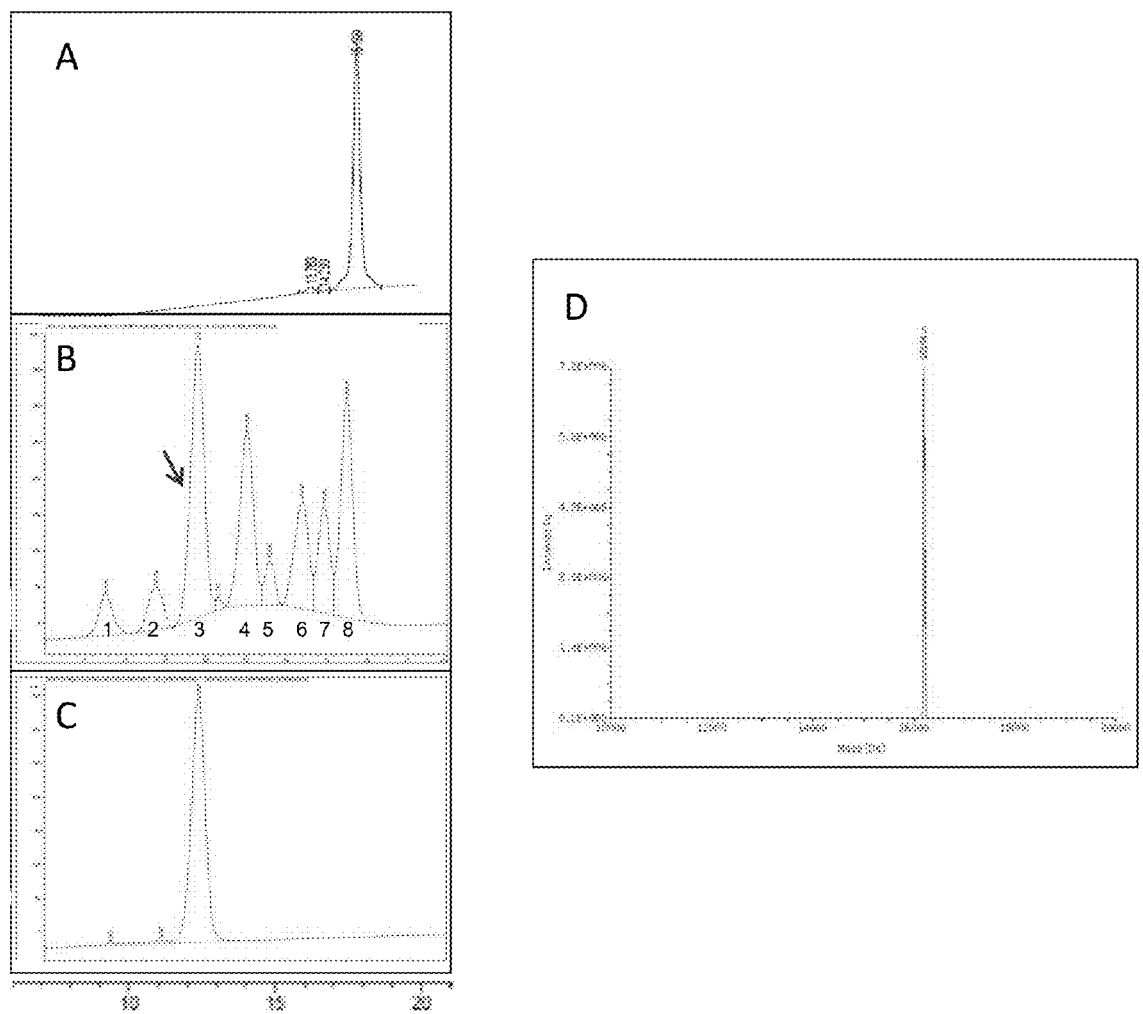
FIG. 11: Purification & mass spectral analysis of mCPBA reaction products: CC10 isoforms. C-18 RP-HPLC was used to separate each of eight individual CC10 isoforms represented as different peaks from the mCBPA reaction mixture. In this example, peak #3 was collected, rerun on the HPLC to estimate purity, then sent for mass spectral analysis (electrospray ionization method). The arrow points out the peak that was purified in this example. All samples contain ~25 mcg protein. Results of ESI-MS analysis are shown in Panel D.

In order to further characterize the CC10 isoforms generated in the mCPBA reaction, a protein sample of each of 8 separate major HPLC peaks (numbered 1-8) was collected, concentrated using a Speedvac, and verified by repeat HPLC to represent a single peak; for example peak 3, as shown in FIG. 11. The samples were then analyzed by electrospray mass spectrometry (ESI-MS) to obtain molecular weights for each isoform. Table 2 shows the results of the MS analysis of isoforms contained in individual HPLC peaks. All CC10 isoforms had a greater molecular weight (MW) than the unmodified form, which has a MW of 16,110 daltons (Da). The addition of an oxygen adds 16 Da. The mCPBA reaction oxidized methionine residues before modifying other amino acids. This is clear since the average mass of 5 of the 8 peaks was increased by a multiple of 16 (eg. peaks 2, 4, 5, 6, and 8). Peak 3 did not increase by an even multiple of 16; this peak contains dimers in which the average number of oxygens is 5.25 or may represent more complex modification than simple addition of oxygen. Peaks 1 and 7 did not yield usable mass spectra.

TABLE 2

Mass spectral analysis of isolated mCPBA CC10 isoforms

| Peak # | Mass (daltons) | Mass change (daltons) | # of Oxygens added |
|---|---|---|---|
| 1 | Not obtained | | |
| 2 | 16206.5 | +~96 | 6 |
| 3 | 16194 | +~84 | 5.25 |
| 4 | 16190.7 | +~80 | 5 |
| 5 | 16174.1 | +~64 | 4 |
| 6 | 16173.5 | +~64 | 4 |
| 7 | Not obtained | | |
| 8 | 16125.1 | +~16 | 1 |

Example 3

Chemical Modification of rhCC10 by ROS: Myeloperoxidase Enzyme (MPO) and Hydrogen Peroxide ($H_2O_2$)

Figure 12:
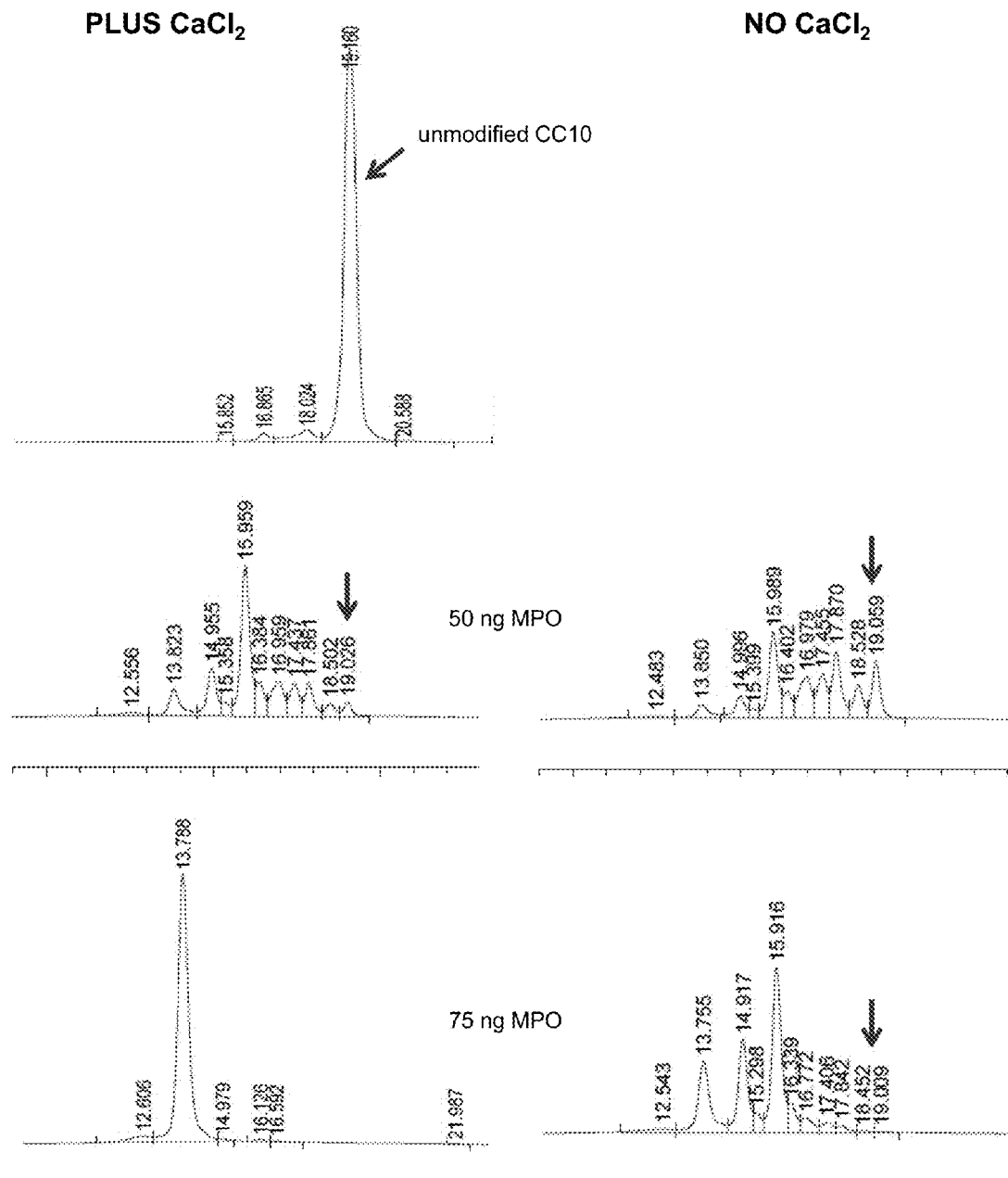
FIG. 12: Optimization of MPO-$H_2O_2$ reaction; Effect of $CaCl_2$. MPO-$H_2O_2$ reactions with and without 2 mM $CaCl_2$ were compared using C-18 RP-HPLC to monitor reactions. All reactions were performed in the dark in citrate buffer at pH 5.0 with 50 oxidant equivalents of $H_2O_2$ at 37° C. for a total of 60 minutes. Arrows point out peaks corresponding to unmodified rhCC10. All samples contain ~25 mcg protein.
Figure 13:
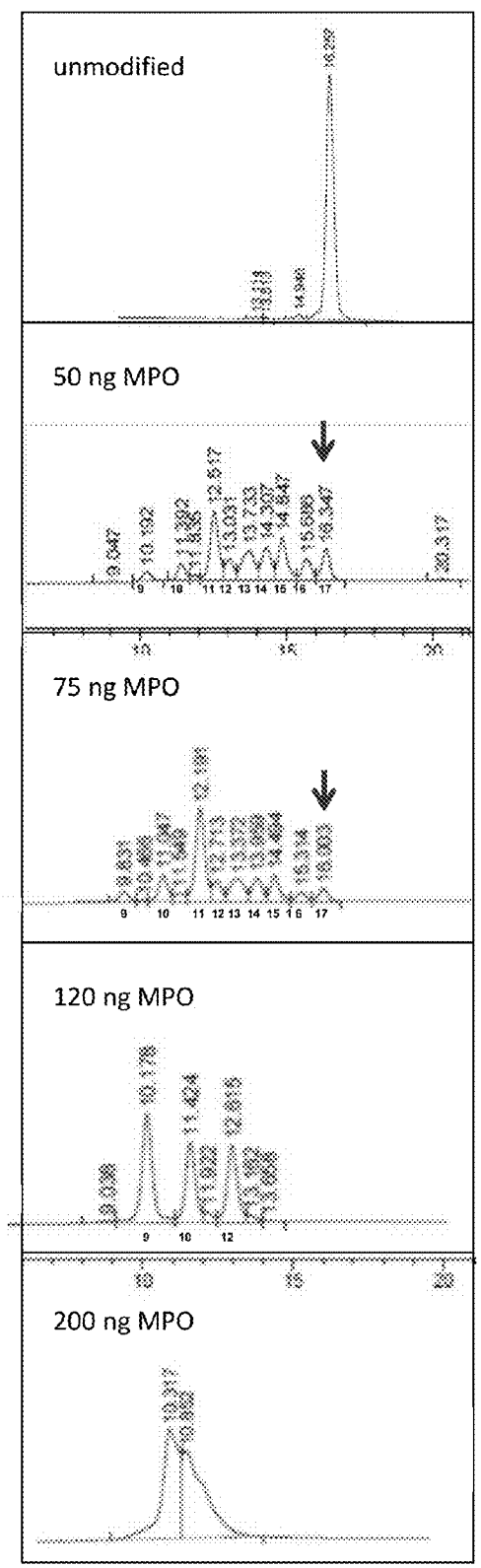
FIG. 13: HPLC analysis of MPO-$H_2O_2$ oxidation products. MPO-$H_2O_2$ reactions with 2 mM $CaCl_2$ were monitored using C-18 RP-HPLC with increasing amounts of MPO and $H_2O_2$. All reactions were performed in the dark in citrate buffer at pH 5.0 with 50 oxidant equivalents of $H_2O_2$ at 37° C. for a total of 30 minutes. Arrows point out peaks corresponding to unmodified rhCC10. All samples contain ~25 mcg protein.

Modification of rhCC10 by MPO plus $H_2O_2$ was monitored using HPLC. The reaction of rhCC10 with MPO-$H_2O_2$ required extensive optimization before any CC10 modifications were observed. Initial reactions performed in phosphate buffered saline (PBS), pH 7.4, in the absence of calcium chloride ($CaCl_2$) were unsuccessful. Very modest increases in the number and height of new HPLC peaks were achieved in phosphate buffer at neutral pH with increasing amounts of MPO and $H_2O_2$. However, the lowering of pH to 5 using citrate buffer and the addition of $CaCl_2$ dramatically increased the CC10 reaction products detectable as new HPLC peaks as shown in FIG. 12. Once calcium was added and pH was optimized, the amounts of MPO and $H_2O_2$ oxidant equivalents were re-optimized and a reproducible HPLC peak pattern showing a clear MPO- and $H_2O_2$-concentration and time dependent peak progression was observed. Briefly, a solution of the protein (0.1 mg, 6.21 nmol) in 2 mM $CaCl_2$ and 10 mM citrate buffer (pH 5) was incubated at 37° C. for 30 min. The reaction was initiated at 37° C. by adding MPO (2.5 µL, 10 µg/mL in water, 25 ng) and $H_2O_2$ (1.55 µL, 100 mM in water, 155.25 nmol, 25 equivalents) and incubated in the dark for 30 min at 37° C. with occasional stirring. Another aliquot of MPO (25 ng) and $H_2O_2$ (1.55 µL) solutions were added and incubated for further 30 min at that temperature with stirring (total volume of 0.2 mL). The reaction was stopped by the addition of L-methionine (4.66 µL; 0.1 M in water, 0.466 µmol) and incubated for 30 min at 37° C. Reactions were typically concentrated in a Speedvac, then resuspended in water, and about 25 µg of each sample was injected onto the HPLC, as with the NaOCl and mCPBA reactions. Modified isoforms appeared as new HPLC peaks, eluting earlier than unmodified rhCC10, as shown in FIG. 13.

Figure 14:
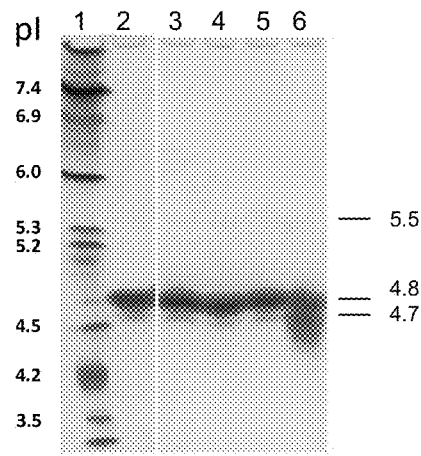
FIG. 14: Isoelectric focusing of rhCC10 MPO and $H_2O_2$ reactions. The IEF gel covered pH range from 3-7. Preparations of rhCC10 modified with increasing amounts of MPO. All reactions were performed in the dark in citrate buffer at pH 5.0 with 50 oxidant equivalents of $H_2O_2$ at 37° C. for a 1 or 24 hours. All samples contain ~25 mcg protein. Samples were not reduced, exposed to SDS, or heated prior to gel loading.
Figure 15:
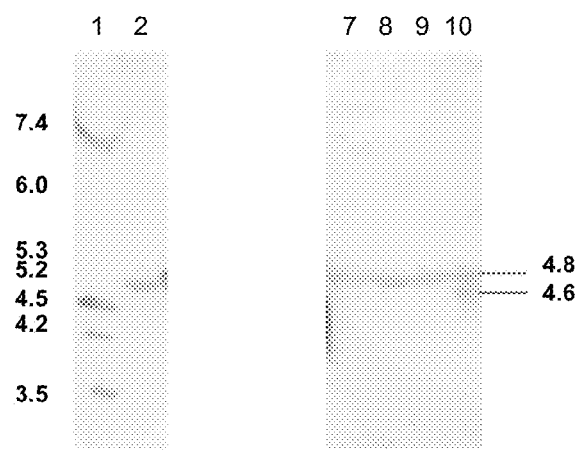
FIG. 15: Western blot of IEF gels of rhCC10 MPO and $H_2O_2$ reactions using anti-rhCC10 antibody. The IEF gel covered pH range from 3-7 and was blotted to PVDF membrane, then probed with Protein-A purified rabbit polyclonal antibody raised against rhCC10. Preparations of rhCC10 modified with increasing amounts of MPO. All reactions were performed in the dark in citrate buffer at pH 5.0 with 50 oxidant equivalents of $H_2O_2$ at 37° C. for a 1 or 24 hours. All samples contain ~25 mcg protein. Samples were not reduced, exposed to SDS, or heated prior to gel loading.

Isoelectric focusing of the MPO and $H_2O_2$ reactions, shown in FIG. 14, revealed that only 2 isoforms with altered isoelectric points were generated, including an isoform at 5.5 and one or more isoforms below 4.7. Unmodified CC10 sometimes appears as a major band at 4.8 plus a minor band at 4.7 in IEF gels (likely dimer and monomer, respectively). The gel was loaded with 25 mcg of each preparation, so that minor bands would not be missed. Therefore, the multiple peaks observed by HPLC (n=8) do not match the number of new bands on IEF (n>2). This indicates that, remarkably, at least 6 of the isoforms separated by HPLC on the basis of hydrophobic interactions retain the same surface charge as unmodified CC10. Western blot of an identical IEF gel, shown in FIG. 15, demonstrated that these pI 4.8 isoforms are recognized by a rabbit polyclonal antibody raised against unmodified rhCC10.

Figure 16:
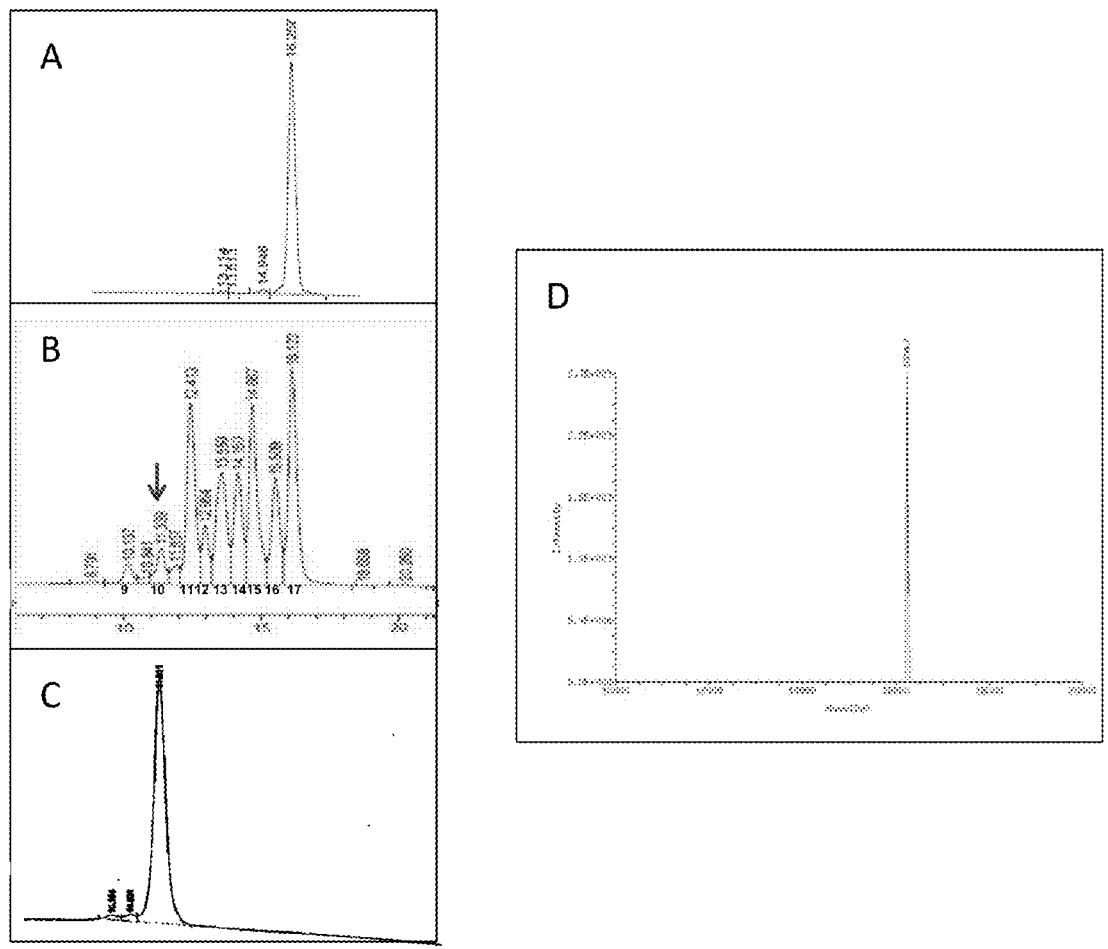
FIG. 16: Purification and mass spectral analysis of a CC10 isoform from a MPO-$H_2O_2$ reaction. C-18 RP-HPLC was used to separate each of eight individual CC10 isoforms represented as different peaks, numbered 9-17, from the MPO-$H_2O_2$ reaction mixture. In this example, peak #10 was collected, rerun on the HPLC to estimate purity, then sent for mass spectral analysis (electrospray ionization method). The arrow points out the peak that was purified in this example. All samples contain ~25 mcg protein. Results of ESI-MS analysis are shown in Panel D.

In order to further characterize the CC10 isoforms generated in the MPO-$H_2O_2$ reactions, a protein sample of each of 8 major separable HPLC peaks (numbered 9-17) was collected, concentrated using a Speedvac, and verified by repeat HPLC to represent a single peak; for example peak 10, as shown in FIG. 16. The samples were then analyzed by electrospray mass spectrometry (ESI-MS) to obtain molecular weights for each isoform. Table 3 shows the results of the MS analysis. All CC10 isoforms had a greater molecular weight (MW) than the unmodified form, which has a MW of 16,110 daltons (Da). In contrast to the mCPBA isoforms, none of the MPO-$H_2O_2$ isoforms showed molecular weight increases that were multiples of 16 (eg. simple additions of oxygen). Modifications under the conditions tested may include some combination of the addition of oxygen, chlorine, or other adducts, as well as the formation of carbonyl groups.

TABLE 3

Mass spectral analysis of isolated MPO-$H_2O_2$ CC10 isoforms

| Peak # | Mass (daltons) | Mass change (daltons) | # of Oxygens added |
|---|---|---|---|
| 9 | Not obtained | | |
| 10 | 16234.7 | 124.7 | 7.79 |
| 11 | 16211.6 | 101.6 | 6.35 |
| 12 | 16218.9 | 108.9 | 6.81 |
| 13 | 16194.3 | 84.3 | 5.27 |
| 14 | 16191.7 | 81.7 | 5.11 |
| 15 | 16171.1 | 61.1 | 3.82 |
| 16 | 16188.1 | 78.1 | 4.88 |
| 17 | 16177 | 67 | 4.19 |

Example 4

Chemical Modification of rhCC10 by RNS: Peroxynitrite

Figure 17:
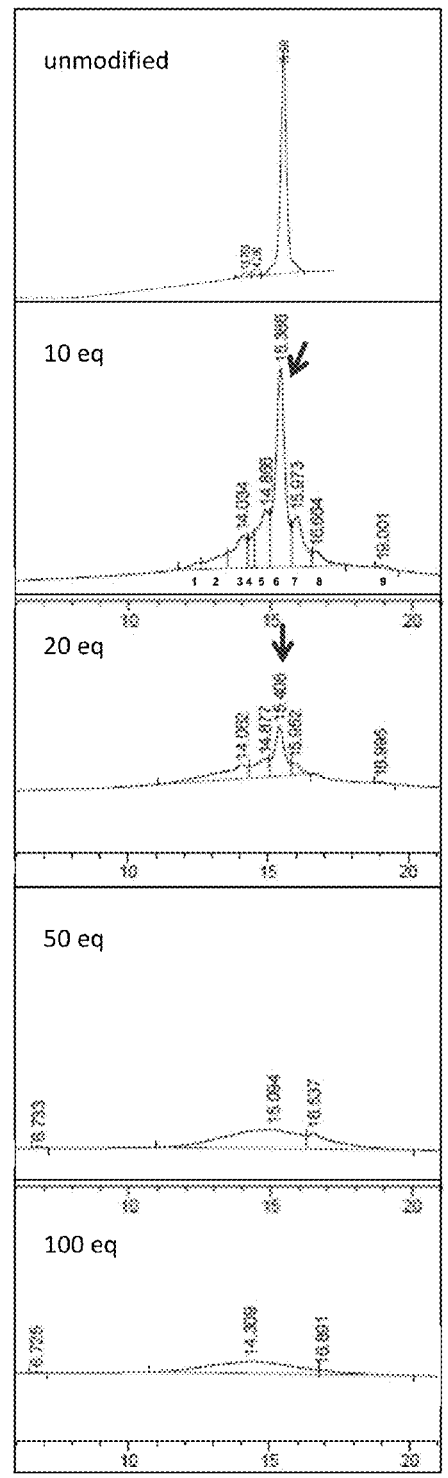
FIG. 17: HPLC analysis of peroxynitrite oxidation products. Reactions of rhCC10 with peroxynitrite were monitored using C-18 RP-HPLC with increasing numbers of oxidant equivalents. Reactions were performed in water at room temperature in the dark for 1 hour. The arrow points out the peak corresponding to unmodified rhCC10. All samples contain ~25 mcg protein.
Figure 18:
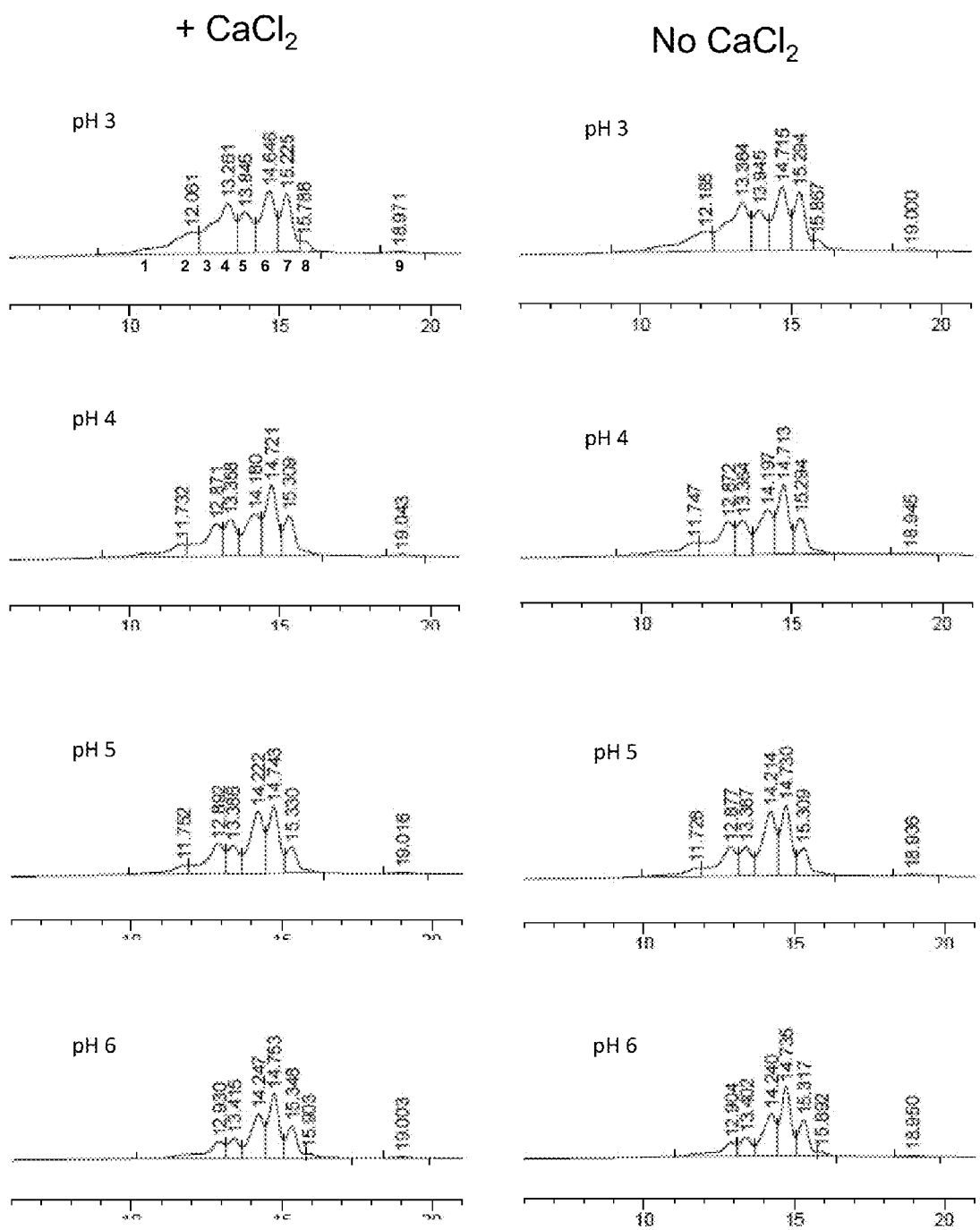
FIG. 18: Effects of pH and $CaCl_2$ on peroxynitrite-mediated oxidation of rhCC10. Reactions of rhCC10 with peroxynitrite in the presence and absence of $CaCl_2$ and at different pHs were monitored using C-18 RP-HPLC with increasing numbers of oxidant equivalents. Reactions were performed using 10 oxidant equivalents at room temperature in the dark for 1 hour. Arrows point out peaks corresponding to unmodified rhCC10. All samples contain ~25 mcg protein.

Modification of rhCC10 by peroxynitrite was monitored using HPLC. Each reaction was initiated at ~23° C. (room temperature) by adding commercially available peroxynitrite reagent (10-100 equivalents) to 0.1 mg of protein (total reaction volume 0.2 mL), stirring briefly and incubating for 1h in the dark. Reactions were typically concentrated in a Speedvac, then resuspended in water, and about 25 μg of each sample was injected onto the HPLC, as with the other reactions. Modified isoforms appeared as new HPLC peaks, eluting both earlier and later than unmodified rhCC10, as shown in FIG. 17. Four new major peaks are evident using 10 equivalents, in addition to a peak that elutes at the same retention time as unmodified CC10. Use of over 20 equivalents resulted in loss of peaks, which broaden into a long bump centered at a point that elutes slightly sooner than unmodified CC10. This broad bump pattern indicates that a vast number of modifications and isoforms are generated. Given the loss of resolution of HPLC peaks, 10 equivalents was the maximum used in further experiments. Further optimization was performed at pH ranging from 3-6 (10 mM citrate buffer), with and without 2 mM $CaCl_2$ as shown in FIG. 18. In contrast to MPO-$H_2O_2$ and mCPBA, where calcium and pH had a significant effect on the reactions, there was no apparent impact on the peroxynitrite reaction products.

Figure 19:
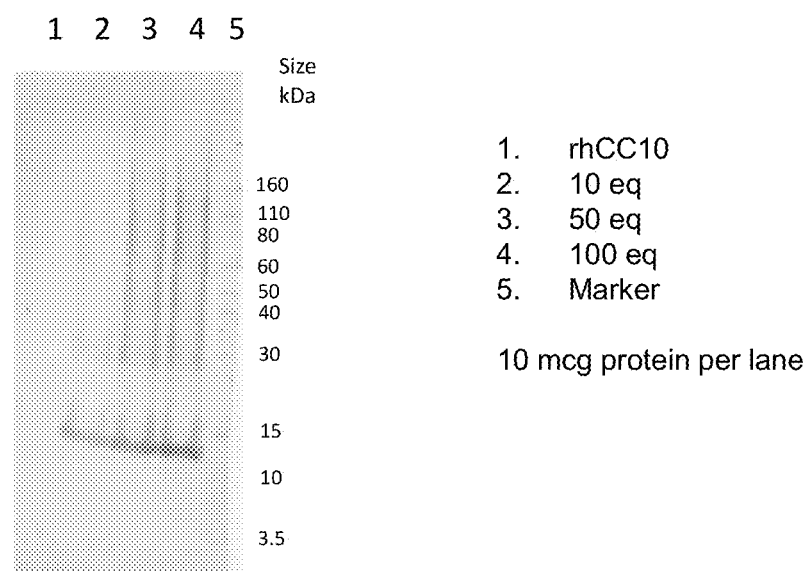
FIG. 19: Western blot analysis of peroxynitrite reaction products. A 10-20% tricine SDS-PAGE gel was run on the modified rhCC10 preparations. The gel was blotted to PVDF then probed with rabbit polyclonal anti-nitrotyrosine antibody (commercially available). Samples containing 10 mcg protein were not reduced but were mixed with SDS PAGE loading buffer and heated to 65° C. for 15 minutes prior to loading. Unmodified rhCC10 was not recognized by the antibody.
Figure 20:
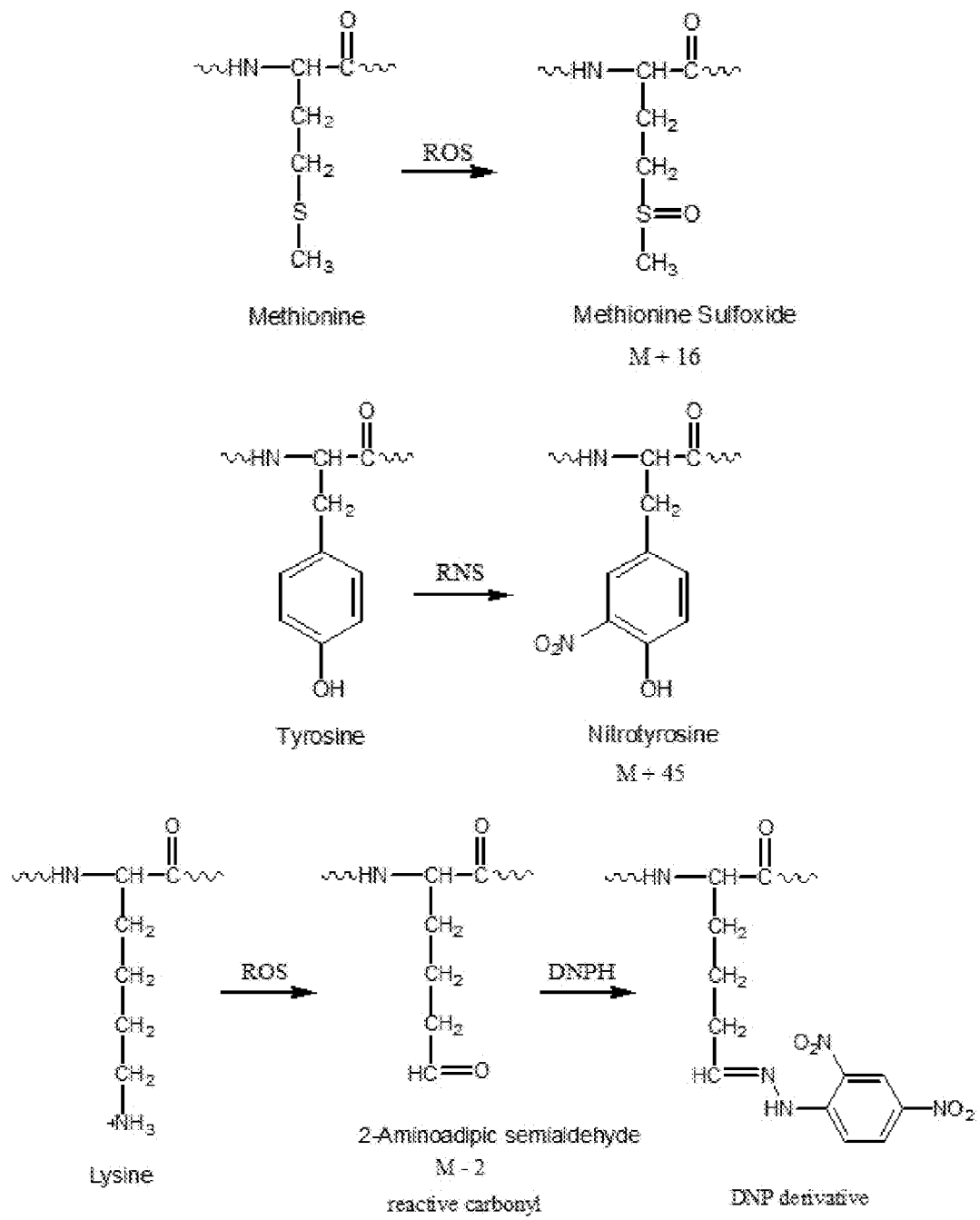
FIG. 20: Secretoglobin reaction products of ROS and RNS detected with rhCC10 protein. Schematic diagrams of oxidative modification reaction products observed with rhCC10; addition of oxygen to methionine, addition of nitro group to tyrosine, formation of carbonyl groups that are reactive with DNPH.

Each CC10 monomer contains a single tyrosine, which these results show is susceptible to nitration in the presence of RNS. As the reaction with peroxynitrite progresses, intermolecular bonds may form di-tyrosine complexes in different monomers. The isoforms generated by the peroxynitrite reactions were largely intact CC10 with larger covalently linked complexes as shown by Western blot of SDS-PAGE in FIG. 19. CC10 peroxynitrite reactions were run under non-reducing conditions in a 1-10% SDS-PAGE tricine gel, which was blotted to PVDF membrane, blocked with 4% non-fat milk, and probed with rabbit polyclonal anti-nitrotyrosine antibody. The blot shows immunoreactive CC10 dimers, tetramers, and "smears" of higher molecular weight complexes, proving that the tyrosine residue in the CC10 monomer is susceptible to modification. Nitration of tyrosine does not disrupt dimer or tetramer stability. This pattern further indicates that tyrosine nitration favors the formation of large complexes, likely linked together by both di-tyrosines and disulfide bonds, but does not generate the distinct sets of thermodynamically favored multimers achieved by simple disulfide bond rearrangements in the absence of di-tyrosine formation.

Example 5

Modification of CC10 by Transglutaminase

Figure 21:
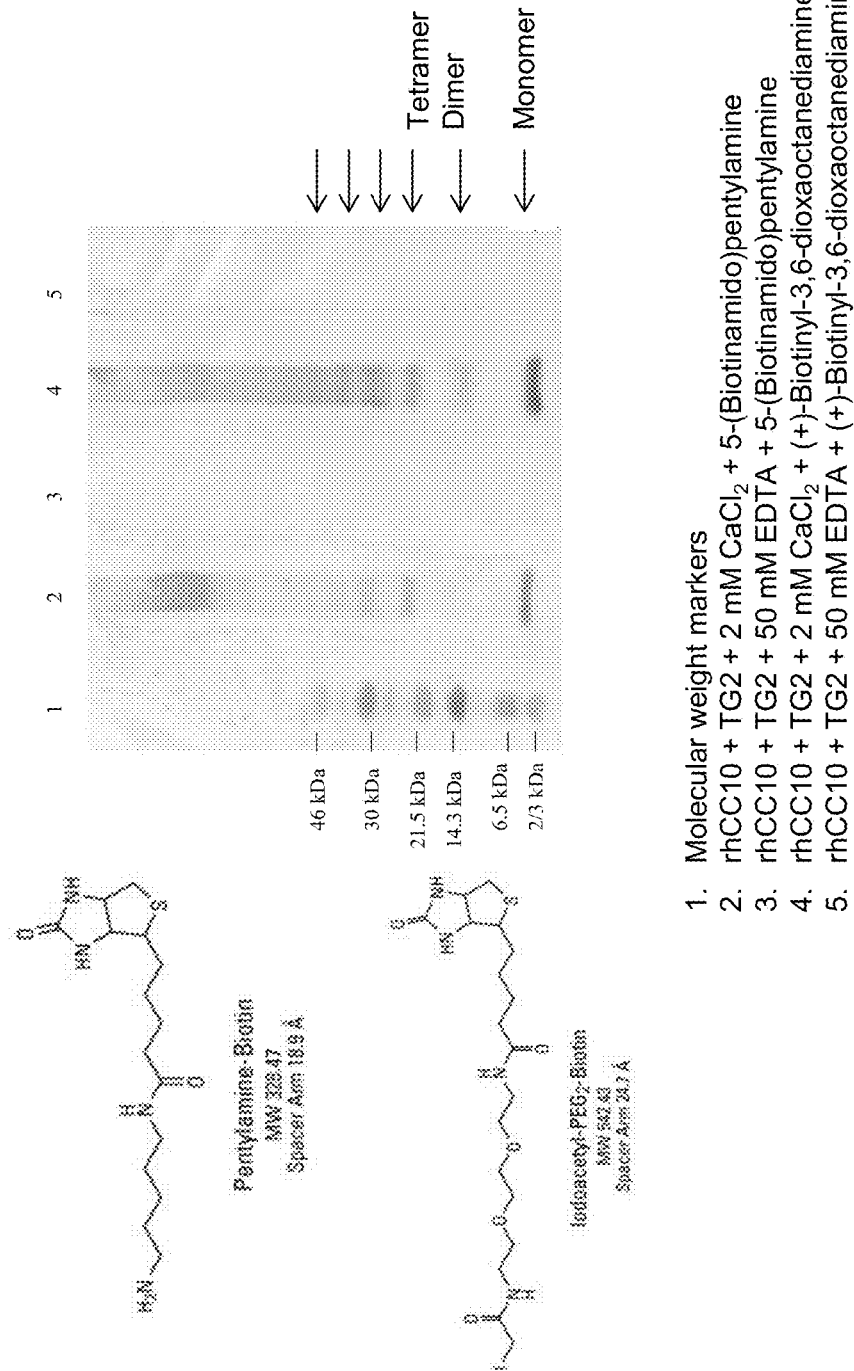
FIG. 21: Modification of rhCC10 by transglutaminase. Western blot of in vitro reactions of rhCC10 using TG2+4.5 mM calcium with two different biotinylated amine compounds. The reactions were performed in 25 mM Tris/150 mM NaCl pH 8.0 with 1.5 mM DTT at using 5 micro-units of TG2 enzyme at 37° C. for 60 minutes. Reactions were run on a 10-20% SDS-PAGE tricine gel, blotted to PVDF membrane, and probed with streptavidin-HRP conjugate, which recognizes the biotin. All lanes contain reducing agent to eliminate disulfide bonds.

CC10 was shown to be an in vitro substrate of tissue transglutaminase (aka TG2) (Manjunath, 1984), and is cross-linked to itself and other proteins via glutamine and lysine residues. Determination of availability of glutamine in uteroglobin as an acyl donor/amine acceptor was performed using biotin linked to two different monoamine groups. Purified guinea pig liver transglutaminase and monoamine-biotin reagents; 5-(Biotinamido)pentylamine and (+)-Biotinyl-3,6-dioxaoctanediamine; were purchased from a commercial vendor. The reactions were performed in 25 mM Tris/150 mM NaCl pH 8.0 with 1.5 mM DTT. Where applicable, $CaCl_2$ was used at a final concentration of 4.5 mM. Calcium is a TG cofactor required for the crosslinking of glutamine and lysine residues. In the absence of calcium and reducing agent, TG2 mediates a rearrangement of disulfide bonds in CC10, resulting in formation of a "ladder" of multimers that can be reduced with a reducing agent (not shown). The protein and amine of interest were combined in buffer with or without calcium to an assay volume of 0.1 mL. Samples were pre-incubated at 37° C. for 30 minutes prior to the addition of the transglutaminase. EDTA at a final concentration of 50 mM was added to the samples without calcium and acted as negative controls. After the pre-incubation 5 μU of transglutaminase was added to each tube and the reaction was allowed to proceed at 37° C. for 60 minutes. After 60 minutes EDTA (50 mM) was added to the tubes containing calcium to stop the reaction. One hundred μL of SDS sample buffer plus reducing agent (1 mM DTT) was added to each reaction, which were then heated at 95° C. for 10 minutes prior to separation on a SDS-PAGE gel. The gel was blotted to a PVDF membrane. Blocking was done for 1 hour at room temperature using 5% BSA (filtered through a 2 micron membrane). Washes between incubations were done with PBS-Tween (0.4%). Biotin groups were detected on the labeled protein(s) by incubating with a streptavidin-alkaline phosphatase conjugate. Visualization was performed with colorimetric reagents (NBT/BCIP) as shown in FIG. 21. The results show that glutamines and lysines in CC10 are both acyl donors and acyl acceptors for TG2 reactions. The reaction is calcium dependent and is abolished by the removal of calcium with a chelating agent. The non-reducible high molecular weight bands indicate that CC10 contains at least two reactive glutamine— lysine pairs, since the high molecular weight bands represent cross-linked CC10 with at least one glutamine-amine biotin amine per complex (such that a single monomer is both labeled with the biotin tag and cross-linked to at least one other monomer). This also illustrates that moieties such as labels, chemicals, lipids, and peptides containing primary amine groups may be added to rhCC10 using TG2 in the presence of calcium and a reducing agent while other moieties containing sulfhydryl groups may be added to rhCC10 using TG in the absence of a reducing agent.

Example 6

Enhanced Inhibition of Influenza Replication In Vitro by Modified rhCC10 Compared to Unmodified rhCC10

Figure 22:
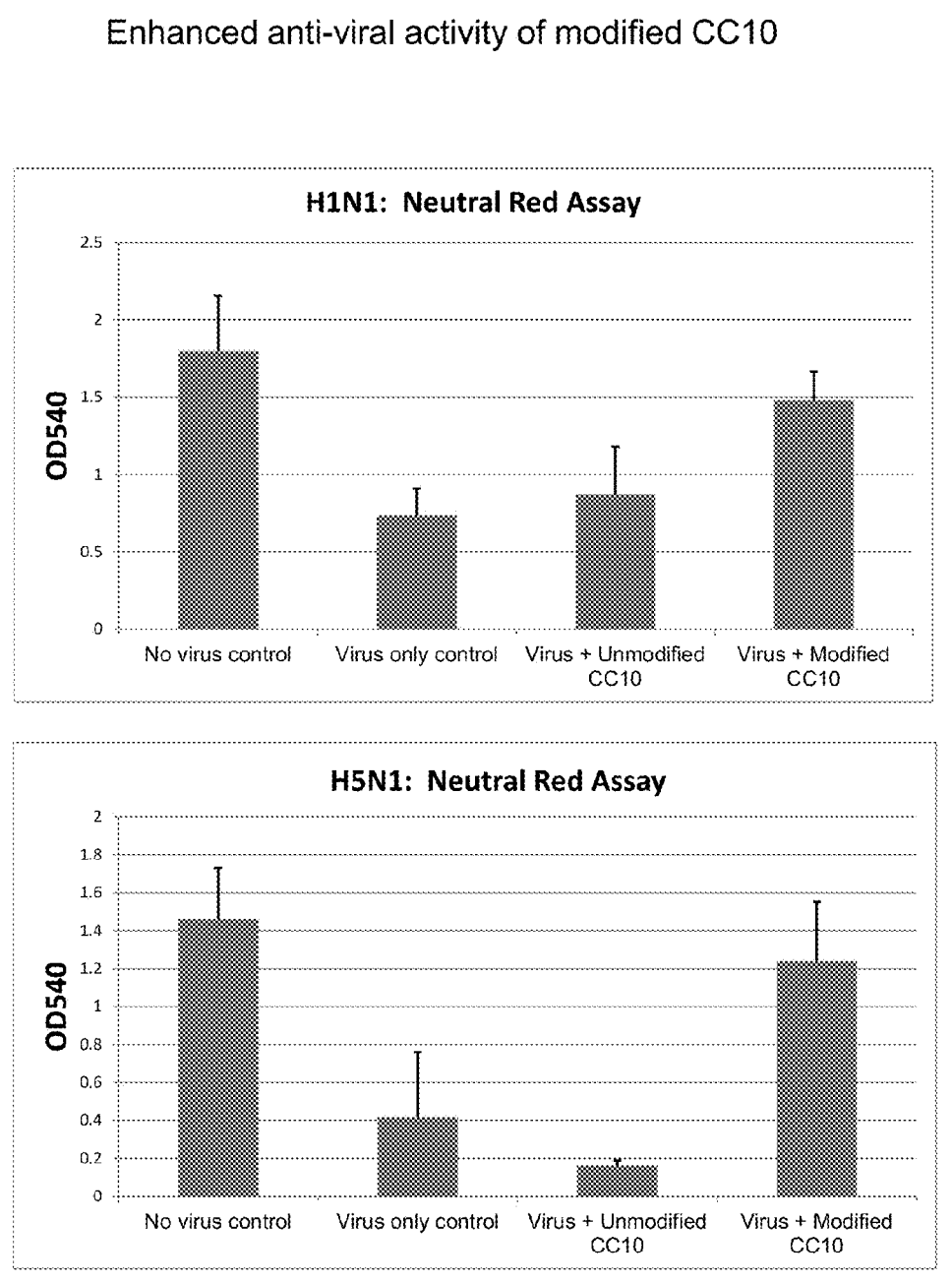

In order to determine the effect of modification on the activity of rhCC10, a single pool of modified rhCC10 was made by combining equal aliquots of rhCC10 reactions with NaOCl, mCPBA, MPO+$H_2O_2$, and peroxynitrite. All HPLC peaks from each reaction were represented in the pool. Modified and unmodified rhCC10 preparations were diluted in eight half-log dilutions in MEM solution at the highest concentrations possible with the sample available. Each dilution was added to 5 wells of a 96-well plate with 80-100% confluent MDCK cells. Three wells of each dilution were infected with virus (H1N1 or H5N1), and two wells remained uninfected as toxicity controls. The multiplicity of infection (MOI) for each virus was between 0.1-1.0. Media was MEM solution with 10 units/mL trypsin. After untreated virus control wells reached maximum cytopathic effect (CPE), plates were then stained with neutral red dye for approximately 2 hours, then supernatant dye was removed from the wells and the incorporated dye was extracted in 50:50 Sorensen citrate buffer/ethanol, then the optical density at 540 nm was read on a spectrophotometer. Neutral red dye is taken up in live cells and used as a measure of cells remaining after viral infection. Results are shown in FIG. 22. Surprisingly, the modified rhCC10 preparation demonstrated enhanced anti-viral activity against two strains of influenza rather than a loss of function that is normally the consequence of oxidative protein modification.

Example 7

Enhanced Inhibition of Neutrophil Chemotaxis In Vitro by Modified rhCC10 Compared to Unmodified rhCC10

Human PLB-985 cells are an immature myeloid leukemia cell line that can be differentiated in vitro essentially into mature human neutrophils (Pedruzzi, 2002). The differentiated PLB-985 cells can then be used as surrogates for actual human neutrophils isolated from peripheral blood in neutrophil function assays such as chemotaxis in response to a variety of stimuli, including fMLP. fMLP is a formylated peptide (Met, Leu, Pro) that is produced only by bacteria and is a signal of bacterial overgrowth to the body that elicits a potent anti-inflammatory response, including migration of neutrophils along a concentration gradient towards the source of the fMLP. Both unmodified and modified rhCC10 were evaluated as inhibitors of differentiated PLB-985 (dPLB-985) in this model.

Cells were grown in RPMI 1640 medium containing 10% FBS, 100 U/ml penicillin, and 100 µg/ml streptomycin at 37° C. in a humidified atmosphere of 5% $CO_2$. To induce a differentiation to the mature neutrophil phenotype, PLB-985 cells were cultured in medium supplemented with 300 µM dibutyril cyclic AMP for 3 days before each experiment. Differentiated PLB-985 cells were resuspended in RPMI-1640 (without phenol red) containing 10% FBS (RPMI/FBS) at $10^7$ cells/mi. The cells were pre-incubated with 5 µg/ml calcein-acetoxymethyl ester at 37° C. for 30 min in the dark with constant agitation. The cells were then washed and resuspended in RPMI/FBS at $2 \times 10^6$ cells/ml. The dPLB-985 cells were incubated with 100 mcg/ml rhCC10 preparations at 37° C. for 60 min or PBS (50%). Cell migration was monitored using a 96-well ChemoTX disposable chemotaxis system (Neuro Probe). The wells of the lower chamber of the plate were filled with 32 µl of fMLP at $10^{-8}$ M. The polycarbonate filters (3 µM) were positioned on the plate, and dPLB-985 cells (30 µl; 60,000 cells/well) were placed on the filter and allowed to migrate for 120 min at 37° C. in the presence of 5% $CO_2$ in the dark. The cells that had not migrated were removed by gently wiping the filters with a tissue.

The fluorescence of the cells in the filters was measured with a microplate fluorescence reader using excitation and emission wavelengths of 485 and 530 nm, respectively. The fluorescence from known numbers of dPLB-985 were obtained by placing them into the bottom chamber and a standard curve was generated (FIG. 23, panel B). FIG. 23 shows that unmodified rhCC10 (CC10-A) slightly inhibits neutrophil migration in response to fMLP, while NaOCl-modified rhCC10 (CC10-B) and mCPBA-modified rhCC10 (CC10-C) both inhibit neutrophil migration to a significantly greater extent. It was surprising to discover that these reactions enhanced rhCC10 activity rather than causing the more typical loss of function that is more often the result of oxidative modification.

DEFINITIONS

Secretoglobin: A type of protein that includes human and non-human proteins in the CC10 family having the conserved four helical bundle motif and ranging in size from about 50-100 amino acids in length. Human secretoglobins are shown in FIG. 1.

Synthetic secretoglobin: A secretoglobin that is made by chemical or recombinant process and not isolated from a natural source.

Unmodified secretoglobin protein: A secretoglobin monomer, dimer, or other multimer that does not contain chemically or enzymatically modified amino acid residues, other than spontaneously occurring disulfide bonds between cysteine residues in homodimers and heterodimers.

Unmodified CC10 protein: A CC10 monomer, dimer, or other multimer that does not contain chemically or enzymatically modified amino acid residues, other than disulfide bonds between cysteine residues.

Modified secretoglobin: A secretoglobin monomer, dimer, or other multimer, that contains one or more chemically or enzymatically modified amino acid residues.

Modified synthetic secretoglobin: A synthetic secretoglobin monomer, dimer, or other multimer, that contains one or more chemically or enzymatically modified amino acid residues.

Modified CC10: A CC10 monomer, dimer, or other multimer, that contains one or more chemically or enzymatically modified amino acid residues.

Modified recombinant human CC10: A CC10 monomer that is made by recombinant DNA methods and contains one or more chemically or enzymatically modified amino acid residues.

Modified synthetic CC10: A CC10 monomer made by either recombinant DNA or chemical peptide synthetic methods that contains one or more chemically or enzymatically modified amino acid residues.

Modified amino acid residues: An amino acid in a protein whose side chain has been modified from the form originally present upon completion of translation of the protein. The chemical structure of the 20 natural unmodified amino acids found in proteins can be found in any biochemistry textbook.

Carbonyl group: An aldehyde or ketone group on an amino acid side chain.

ABBREVIATIONS

CC10: Clara cell 10 kDa protein; aka CC16, CCSP, uteroglobin, urine protein-1
SCGB: Secretoglobin
RNS: reactive nitrogen species
ROS: reactive oxygen species
MPO: myeloperoxidase enzyme
iNOS: intracellular nitric oxide synthase
mCPBA: meta-choloroperbenzoic acid
DNP: 2,4-dinitrophenylhydrazone
DNPH: 2,4-dinitrophenylhydrazine
HNE: 4-hydroxy-2-trans-nonenal (HNE); a lipid peroxidation product
MDA: malanodialdehyde While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

---

We claim:

1. A composition of matter comprising a chemically or enzymatically oxidized synthetic CC10 having one or more nitrotyrosines.

2. The composition of claim 1 wherein the chemically or enzymatically oxidized synthetic CC10 further comprises one or more methionine sulfoxides.

3. The composition of claim 1 wherein the chemically or enzymatically oxidized synthetic CC10 further comprises one or more chlorotyrosines or di-tyrosines.

4. The composition of claim 1 wherein the chemically or enzymatically oxidized synthetic CC10 further comprises one or more cysteine glutathiolates or HNE-cysteines.

5. The composition of claim 1 wherein the chemically or enzymatically oxidized synthetic CC10 further comprises carbonyl groups in excess of those present in unmodified CC10.

6. The composition of claim 1 wherein the chemically or enzymatically oxidized synthetic CC10 further comprises one or more hydroxyprolines or pyrrolidines.

7. The composition of claim 1 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

8. The composition of claim 1 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

9. The composition of claim 1 wherein the chemically or enzymatically oxidized synthetic CC10 further comprises one or more labels, chemicals, lipids, or peptides attached to a glutamine or lysine residue.

10. A composition of matter comprising a chemically or enzymatically oxidized synthetic CC10 having one or more chlorotyrosines.

11. The composition of claim 10 wherein the chemically or enzymatically oxidized synthetic CC10 further comprises one or more methionine sulfoxides.

12. The composition of claim 10 wherein the chemically or enzymatically oxidized synthetic CC10 further comprises one or more nitrotyrosines or di-tyrosines.

13. The composition of claim 10 wherein the chemically or enzymatically oxidized synthetic CC10 further comprises one or more cysteine glutathiolates or HNE-cysteines.

14. The composition of claim 10 wherein the chemically or enzymatically oxidized synthetic CC10 further comprises carbonyl groups in excess of those present in unmodified CC10.

15. The composition of claim 10 wherein the chemically or enzymatically oxidized synthetic CC10 further comprises one or more hydroxyprolines or pyrrolidines.

16. The composition of claim 10 wherein the chemically or enzymatically synthetic CC10 further comprises one or more α-aminoadipic semialdehydes, chloramines, MDA-Lys, HNE-Lys, acrolein-Lys, carboxymethyllysines, or pHA-Lys.

17. The composition of claim 10 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

18. The composition of claim 10 wherein the chemically or enzymatically oxidized synthetic CC10 further comprises one or more labels, chemicals, lipids, or peptides attached to a glutamine or lysine residue.

19. A composition of matter comprising a chemically or enzymatically oxidized synthetic CC10 having one or more di-tyrosines.

20. The composition of claim 19 wherein the chemically or enzymatically oxidized synthetic CC10 further comprises one or more methionine sulfoxides.

21. The composition of claim 19 wherein the chemically or enzymatically oxidized synthetic CC10 further comprises one or more nitrotyrosines or chlorotyrosines.

22. The composition of claim 19 wherein the chemically or enzymatically oxidized synthetic CC10 further comprises one or more cysteine glutathiolates or HNE-cysteines.

23. The composition of claim 19 wherein the chemically or enzymatically oxidized synthetic CC10 further comprises carbonyl groups in excess of those present in unmodified CC10.

24. The composition of claim 19 wherein the chemically or enzymatically oxidized synthetic CC10 further comprises one or more hydroxyprolines or pyrrolidines.

25. The composition of claim 19 wherein the chemically or enzymatically oxidized synthetic CC10 further comprises one or more α-aminoadipic serniaidehydes, chloramines, MDA-Lys, HNE-Lys, acrolein-Lys, carboxymethyllysines, or pHA-Lys.

26. The composition of claim 19 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

27. The composition of claim 19 wherein the chemically or enzymatically oxidized synthetic CC10 further comprises one or more labels, chemicals, lipids, or peptides attached to a glutamine or lysine residue.

28. A composition of matter comprising a chemically or enzymatically oxidized synthetic CC10 having one or more cysteine glutathiolates.

29. The composition of claim 28 wherein the chemically or enzymatically oxidized synthetic CC10 further comprises one or more methionine sulfoxides.

30. The composition of claim 28 wherein the chemically or enzymatically oxidized synthetic CC10 further comprises one or more nitrotyrosines, chlorotyrosines, or di-tyrosines.

31. The composition of claim 28 wherein the chemically or enzymatically oxidized synthetic CC10 further comprises one or more HNE-cysteines.

32. The composition of claim 28 wherein the chemically or enzymatically oxidized synthetic CC10 further comprises carbonyl groups in excess of those present in unmodified CC10.

33. The composition of claim 28 wherein the chemically or enzymatically oxidized synthetic CC10 further comprises one or more hydroxyprolines or pyrrolidines.

34. The composition of claim 28 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

35. The composition of claim 28 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

36. The composition of claim 28 wherein the chemically or enzymatically oxidized synthetic CC10 further comprises one or more labels, chemicals, lipids, or peptides attached to a glutamine or lysine residue.

37. A composition of matter comprising a chemically or enzymatically oxidized synthetic CC10 having one or more HNE-cysteines.

38. The composition of claim 37 wherein the chemically or enzymatically oxidized synthetic CC10 further comprises one or more methionine sulfoxides.

39. The composition of claim 37 wherein the chemically or enzymatically oxidized synthetic CC10 further comprises one or more nitrotyrosines, chlorotyrosines, or di-tyrosines.

40. The composition of claim 37 wherein the chemically or enzymatically oxidized synthetic CC10 further comprises one or more cysteine glutathiolates.

41. The composition of claim 37 wherein the chemically or enzymatically oxidized synthetic CC10 further comprises carbonyl groups in excess of those present in unmodified CC10.

42. The composition of claim 37 wherein the chemically or enzymatically oxidized synthetic CC10 further comprises one or more hydroxyprolines or pyrrolidines.

43. The composition of claim 37 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

44. The composition of claim 37 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

45. The composition claim 37 wherein the chemically or enzymatically oxidized synthetic CC10 further comprises one or more labels, chemicals, lipids, or peptides attached to a glutamine or lysine residue.

46. A composition of matter comprising a chemically or enzymatically oxidized synthetic CC10 having one or more hydroxyprolines.

47. The composition of claim 46 wherein the chemically or enzymatically oxidized synthetic CC10 further comprises one or more methionine sulfoxides.

48. The composition of claim 46 wherein the chemically or enzymatically oxidized synthetic CC10 further comprises one or more nitrotyrosines, chlorotyrosines, or di-tyrosines.

49. The composition of claim 46 wherein the chemically or enzymatically oxidized synthetic CC10 further comprises one or more cysteine glutathiolates or HNE-cysteines.

50. The composition of claim 46 wherein the chemically or enzymatically oxidized synthetic CC10 further comprises carbonyl groups in excess of those present in unmodified CC10.

51. The composition of claim 46 wherein the chemically or enzymatically oxidized synthetic CC10 further comprises one or more pyrrolidines.

52. The composition of claim 46 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

53. The composition of claim 46 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

54. The composition claim 46 wherein the chemically or enzymatically oxidized synthetic CC10 further comprises one or more labels, chemicals, lipids, or peptides attached to a glutamine or lysine residue.

55. A composition of matter comprising a chemically or enzymatically oxidized synthetic CC10 having one or more pyrrolidines.

56. The composition of claim 55 wherein the chemically or enzymatically oxidized synthetic CC10 further comprises one or more methionine sulfoxides.

57. The composition of claim 55 wherein the chemically or enzymatically oxidized synthetic, CC10 further comprises one or more nitrotyrosines, chlorotyrosines, or di-tyrosines.

58. The composition of claim 55 wherein the chemically or enzymatically oxidized synthetic CC10 further comprises one or more cysteine glutathiolates or HNE-cysteines.

59. The composition of claim 55 wherein the chemically or enzymatically oxidized synthetic CC10 further comprises carbonyl groups in excess of those present in unmodified CC10.

60. The composition of claim 55 wherein the chemically or enzymatically oxidized synthetic CC10 further comprises one or more hydroxyprolines.

61. The composition of claim 55 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

62. The composition of claim 55 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

63. The composition claim 55 wherein the chemically or enzymatically oxidized synthetic CC10 further comprises one or more labels, chemicals, lipids, or peptides attached to a glutamine or lysine residue.

64. A composition of matter comprising a chemically or enzymatically oxidized synthetic CC10 having one or more α-aminoadipic semialdehydes.

65. The composition of claim 64 wherein the chemically or enzymatically oxidized synthetic CC10 further comprises one or more methionine sulfoxides.

66. The composition of claim 64 wherein the chemically or enzymatically oxidized synthetic CC10 further comprises one or more nitrotyrosines, chlorotyrosines, or di-tyrosines.

67. The composition of claim 64 wherein the chemically or enzymatically oxidized synthetic CC10 further comprises one or more cysteine glutathiolates or HNE-cysteines.

68. The composition of claim 64 wherein the chemically or enzymatically oxidized synthetic CC10 further comprises carbonyl groups in excess of those present in unmodified CC10.

69. The composition of claim 64 wherein the chemically or enzymatically oxidized synthetic CC10 further comprises one or more hydroxprolines.

70. The composition of claim 64 wherein the chemically or enzymatically oxidized synthetic CC10 further comprises one or more chloramines, MDA-Lys, HNE-Lys, acrolein-Lys, carboxymethyllysines, or pHA-Lys.

71. The composition of claim 64 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

72. The composition of claim 64 wherein the chemically or enzymatically oxidized synthetic CC10 further comprises one or more labels, chemicals, lipids, or peptides attached to a glutamine or lysine residue.

73. A composition of matter comprising a chemically or enzymatically oxidized synthetic CC10 having one or more chloramines.

74. The composition of claim 73 wherein the chemically or enzymatically oxidized synthetic CC10 further comprises one or more methionine sulfoxides.

75. The composition of claim 73 wherein the chemically or enzymatically oxidized synthetic, CC10 further comprises one or more nitrotyrosines, chlorotyrosines, or di-tyrosines.

76. The composition of claim 73 wherein the chemically or enzymatically oxidized synthetic CC10 further comprises one or more cysteine glutathiolates or HNE-cysteines.

77. The composition of claim 73 wherein the chemically or enzymatically oxidized synthetic CC10 further comprises carbonyl groups in excess of those present in unmodified CC10.

78. The composition of claim 73 wherein the chemically or enzymatically oxidized synthetic CC10 further comprises one or more hydroxyprolines.

79. The composition of claim 73 wherein the chemically or enzymatically oxidized synthetic CC10 further comprises one or more α-aminoadipic semialdehydes, MDA-Lys, HNE-Lys, acrolein-Lys, carboxymethyllysines, or pHA-Lys.

80. The composition of claim 73 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

81. The composition claim 73 wherein the chemically or enzymatically oxidized synthetic CC10 further comprises one or more labels, chemicals, lipids, or peptides attached to a glutamine or lysine residue.

82. A composition of matter comprising a chemically or enzymatically oxidized synthetic CC10 having one or more MDA-Lys.

83. The composition of claim 82 wherein the chemically or enzymatically oxidized synthetic CC10 further comprises one or more methionine sulfoxides.

84. The composition of claim 82 wherein the chemically or enzymatically oxidized synthetic, CC10 further comprises one or more nitrotyrosines, chlorotyrosines, di-tyrosines.

85. The composition of claim 82 wherein the chemically or enzymatically oxidized synthetic CC10 further comprises one or more cysteine glutathiolates or HNE-cysteines.

86. The composition of claim 82 wherein the chemically or enzymatically oxidized synthetic CC10 further comprises carbonyl groups in excess of those present in unmodified CC10.

87. The composition of claim 82 wherein the chemically or enzymatically oxidized synthetic CC10 further comprises one or more hydroxyprolines.

88. The composition of claim 82 wherein the chemically or enzymatically oxidized synthetic CC10 further comprises one or more α-aminoadipic semialdehydes, chloramines, HNE-Lys, acrolein-Lys, carboxymethyllysines, or pHA-Lys.

89. The composition of claim 82 wherein the chemically or enzymatically oxidized synthetic CC10 further comprises one or more 2-amino-3- ketobutyric acids, chloramines, valine peroxides, leucine peroxides, oxalic acids, pyruvic acids, or hydroxyphenylalanines.

90. The composition of claim 82 wherein the chemically or enzymatically oxidized synthetic CC10 further comprises one or more labels, chemicals, lipids, or peptides attached to a glutamine or lysine residue.

91. A composition of matter comprising a chemically or enzymatically oxidized synthetic CC10 having one or more HNE-Lys.

92. The composition of claim 91 wherein the chemically or enzymatically oxidized synthetic CC10 further comprises one or more methionine sulfoxides.

93. The composition of claim 91 wherein the chemically or enzymatically oxidized synthetic CC10 further comprises one or more nitrotyrosines, chlorotyrosines, or di-tyrosines.

94. The composition of claim 91 wherein the chemically or enzymatically oxidized synthetic CC10 further comprises one or more cysteine gluathiolates or HNE-cysteines.

95. The composition of claim 91 wherein the chemically or enzymatically oxidized synthetic CC10 further comprises carbonyl groups in excess of those present in unmodified CC10.

96. The composition of claim 91 wherein the chemically or enzymatically oxidized synthetic CC10 further comprises one or more hydroxyprolines.

97. The composition of claim 91 wherein the chemically or enzymatically oxidized synthetic CC10 further comprises one or more α-aminoadipic semialdehydes, chloramines, MDA-Lys, acrolein-Lys, carboxymethyllysines, or pHA-Lys.

98. The composition of claim 91 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

99. The composition of claim 91 wherein the chemically or enzymatically oxidized synthetic CC10 further comprises one or more labels, chemicals, lipids, or peptides attached to a glutamine car lysine residue.

100. A composition of matter comprising a chemically or enzymatically oxidized synthetic CC10 having one or more acrolein-Lys.

101. The composition of claim 100 wherein the chemically or enzymatically oxidized synthetic CC10 further comprises one or more methionine sulfoxides.

102. The composition of claim 100 wherein the chemically or enzymatically oxidized synthetic CC10 further comprises one or more nitrotyrosines, chlorotyrosines, or di-tyrosines.

103. The composition of claim 100 wherein the chemically or enzymatically oxidized synthetic CC10 further comprises one or more cysteine glutathiolates or HNE-cysteines.

104. The composition of claim 100 wherein the chemically or enzymatically oxidized synthetic CC10 further comprises carbonyl groups in excess of those present in unmodified CC10.

105. The composition of claim 100 wherein the chemically or enzymatically oxidized synthetic CC10 further comprises one or more hydroxyprolines.

106. The composition of claim 100 wherein the chemically or enzymatically oxidized synthetic CC10 further comprises one or more α-aminoadipic semialdehydes, chloramines, MDA-Lys, NNE-Lys, carboxymethyllysines, or pHA-Lys.

107. The composition of claim 100 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

108. The composition of claim 100 wherein the chemically or enzymatically oxidized synthetic CC10 further comprises one or more labels, chemicals, lipids, or peptides attached to a glutamine or lysine residue.

109. A composition of matter comprising a chemically or enzymatically oxidized synthetic CC10 having one or more carboxymethyllysines.

110. The composition of claim 109 wherein the chemically or enzymatically oxidized synthetic CC10 further comprises one or more methionine sulfoxides.

111. The composition of claim 109 wherein the chemically or enzymatically oxidized synthetic CC10 further comprises one or more nitrotyrosines, chlorotyrosines, or di-tyrosines.

112. The composition of claim 109 wherein the chemically or enzymatically oxidized synthetic CC10 further comprises one or more cysteine glutathiolates or HNE-cysteines.

113. The composition of claim 109 wherein the chemically or enzymatically oxidized synthetic CC10 further comprises carbonyl groups in excess of those present in unmodified CC10.

114. The composition of claim 109 wherein the chemically or enzymatically oxidized synthetic CC10 further comprises one or more hydroxyprolines.

115. The composition of claim 109 wherein the chemically or enzymatically oxidized synthetic CC10 further comprises one or more α-aminoadipic semialdehydes, chloramines, MDA-Lys, HNE-Lys, acrolein-Lys, or pHA-Lys.

116. The composition of claim 109 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

117. The composition of claim 109 wherein the chemically or enzymatically oxidized synthetic CC10 further comprises one or more labels, chemicals, lipids, or peptides attached to a glutamine or lysine residue.

118. A composition of matter comprising a chemically or enzymatically oxidized synthetic CC10 having one or more pHA-Lys.

119. The composition of claim 118 wherein the chemically or enzymatically oxidized synthetic CC10 further comprises one or more methionine sulfoxides.

120. The composition of claim 118 wherein the chemically or enzymatically oxidized synthetic CC10 further comprises one or more nitrotyrosines, chlorotyrosines, or di-tyrosines.

121. The composition of claim 118 wherein the chemically or enzymatically oxidized synthetic CC10 further comprises one or more cysteine glutathiolates or HNE-cysteines.

122. The composition of claim 118 wherein the chemically or enzymatically oxidized synthetic CC10 further comprises carbonyl groups in excess of those present in unmodified CC10.

123. The composition of claim 118 wherein the chemically or enzymatically oxidized synthetic CC10 further comprises one or more hydroxyprolines.

124. The composition of claim 118 wherein the chemically or enzymatically oxidized synthetic CC10 further comprises one or more α-aminoadipic semialdehydes, chloramines, MDA-Lys, HNE-Lys, acrolein-Lys, or carboxymethyllysines.

125. The composition of claim 118 wherein the chemically or enzymatically oxidized synthetic CC10 further comprises one or more 2-amino-3-ketobutyric acids, chloramines, valine peroxides, leucine peroxides, oxalic acids, pyruvic acids, or hydroxyphenylalanines.

126. The composition of claim 118 wherein the chemically or enzymatically oxidized synthetic CC10 further comprises one or more labels, chemicals, lipids, or peptides attached to a glutamine car lysine residue.

127. A composition of matter comprising a chemically or enzymatically oxidized synthetic CC10 having one or more 2-amino-3-ketobutyric acids.

128. The composition of claim 127 wherein the chemically or enzymatically oxidized synthetic CC10 further comprises one or more methionine sulfoxides.

129. The composition of claim 127 wherein the chemically or enzymatically oxidized synthetic CC10 further comprises one or more nitrotyrosines, chlorotyrosines, or di-tyrosines.

130. The composition of claim 127 wherein the chemically or enzymatically oxidized synthetic CC10 further comprises one or more cysteine glutathiolates or HNE-cysteines.

131. The composition of claim 127 wherein the chemically or enzymatically oxidized synthetic CC10 further comprises carbonyl groups in excess of those present in unmodified CC10.

132. The composition of claim 127 wherein the chemically or enzymatically oxidized synthetic CC10 further comprises one or more hydroxyprolines.

133. The composition of claim 127 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

134. The composition of claim 127 wherein the chemically or enzymatically oxidized synthetic CC10 further comprises one or more chloramines, valine peroxides, leucine peroxides, oxalic acids, pyruyic acids, or hydroxyphenylalanines.

135. The composition of claim 127 wherein the chemically or enzymatically oxidized synthetic CC10 further comprises one or more labels, chemicals, lipids, or peptides attached to a glutamine or lysine residue.

136. A composition of matter comprising a chemically or enzymatically oxidized synthetic CC10 having one or more valine peroxides.

137. The composition of claim 136 wherein the chemically or enzymatically oxidized synthetic CC10 further comprises one or more methionine sulfoxides.

138. The composition of claim 136 wherein the chemically or enzymatically oxidized synthetic CC10 further comprises one or more nitrotyrosines, chlorotyrosines, or di-tyrosines.

139. The composition of claim 136 wherein the chemically or enzymatically oxidized synthetic CC10 further comprises one or more cysteine glutathiolates or HNE-cysteines.

140. The composition of claim 136 wherein the chemically or enzymatically oxidized synthetic CC10 further comprises carbonyl groups in excess of those present in unmodified CC10.

141. The composition of claim 136 wherein the chemically or enzymatically oxidized synthetic CC10 further comprises one or more hydroxyprolines.

142. The composition of claim 136 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

143. The composition of claim 136 wherein the chemically or enzymatically oxidized synthetic CC10 further comprises one or more 2-amino-3-ketobutyric acids, chloramines, leucine peroxides, oxalic acids, pyruvic acids, or hydroxyphenylalanines.

144. The composition of claim 136 wherein the chemically or enzymatically oxidized synthetic CC10 further comprises one or more labels, chemicals, lipids, or peptides attached to a glutamine or lysine residue.

145. A composition of matter comprising a chemically or enzymatically oxidized synthetic CC10 having one or more leucine peroxides.

146. The composition of claim 145 wherein the chemically or enzymatically oxidized synthetic CC10 further comprises one or more methionine sulfoxides.

147. The composition of claim 145 wherein the chemically or enzymatically oxidized synthetic CC10 further comprises one or more nitrotyrosines, chlorotyrosines, di-tyrosines.

148. The composition of claim 145 wherein the chemically or enzymatically oxidized synthetic CC10 further comprises one or more cysteine glutathiolates or HNE-cysteines.

149. The composition of claim 145 wherein the chemically or enzymatically oxidized synthetic CC10 further comprises carbonyl groups in excess of those present in unmodified CC10.

150. The composition of claim 145 wherein the chemically or enzymatically oxidized synthetic CC10 further comprises one or more hydroxyprolines.

151. The composition of claim 145 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

152. The composition of claim 145 wherein the chemically or enzymatically oxidized synthetic CC10 further comprises one or more 2-amino-3-ketobutyric acids, chloramines, valine peroxides, oxalic acids, pyruvic acids, or hydroxyphenylalanines.

153. The composition of claim 145 wherein the chemically or enzymatically oxidized synthetic CC10 further comprises one or more labels, chemicals, lipids, or peptides attached to a glutamine or lysine residue.

154. A composition of matter comprising a chemically or enzymatically oxidized synthetic CC10 having one or more oxalic acids.

155. The composition of claim 154 wherein the chemically or enzymatically oxidized synthetic CC10 further comprises one or more methionine sulfoxides.

156. The composition of claim 154 wherein the chemically or enzymatically oxidized synthetic CC10 further comprises one or more nitrotyrosines, chlorotyrosines, di-tyrosines.

157. The composition of claim 154 wherein the chemically or enzymatically oxidized synthetic CC10 further comprises one or more cysteine glutathiolates or HNE-cysteines.

158. The composition of claim 154 wherein the chemically or enzymatically oxidized synthetic CC10 further compirses carbonyl groups in excess of those present in unmodified CC10.

159. The composition of claim 154 wherein the chemically or enzymatically oxidized synthetic CC10 further comprises one or more hydroxyprolines.

160. The composition of claim 154 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

161. The composition of claim 154 wherein the chemically or enzymatically oxidized synthetic CC10 further comprises one or more 2-amino-3-ketobutyric acids, chloramines, valine peroxides, leucine peroxides, pyruvic acids, or hydroxyphenylalanines.

162. The composition of claim 154 wherein the chemically or enzymatically oxidized synthetic CC10 further comprises one or more labels, chemicals, lipids, or peptides attached to a glutamine or lysine residue.

163. A composition of matter comprising a chemically or enzymatically oxidized synthetic CC10 having one or more pyruvic acids.

164. The composition of claim 163 wherein the chemically or enzymatically oxidized synthetic CC10 further comprises one or more methionine sulfoxides.

165. The composition of claim 163 wherein the chemically or enzymatically oxidized synthetic CC10 further comprises one or more nitrotyrosines, chlorotyrosines, di-tyrosines.

166. The composition of claim 163 wherein the chemically or enzymatically oxidized synthetic CC10 further comprises one or more cysteine glutathiolates or HNE-cysteines.

167. The composition of claim 163 wherein the chemically or enzymatically oxidized synthetic CC10 further comprises carbonyl groups in excess of those present in unmodified CC10.

168. The composition of claim 163 wherein the chemically or enzymatically oxidized synthetic CC10 further comprises one or more hydroxyprolines.

169. The composition of claim 163 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

170. The composition of claim 163 wherein the chemically or enzymatically oxidized synthetic CC10 further comprises one or more 2-amino-3-ketobutyric acids, chloramines, valine peroxides, leucine peroxides, oxalic acids, or hydroxyphenylalanines.

171. The composition of claim 163 wherein the chemically or enzymatically oxidized synthetic CC10 further comprises one or more labels, chemicals, lipids, or peptides attached to a glutamine or lysine residue.

172. A composition of matter comprising a chemically or enzymatically oxidized synthetic CC10 having one or more hydroxyphenylalanines.

173. The composition of claim 172 wherein the chemically or enzymatically oxidized synthetic CC10 further comprises one or more methionine sulfoxides.

174. The composition of claim 172 wherein the chemically or enzymatically oxidized synthetic CC10 further comprises one or more nitrotyrosines, chlorotyrosines, di-tyrosines.

175. The composition of claim 172 wherein the chemically or enzymatically oxidized synthetic CC10further comprises one or more cysteine glutathiolates or HNE-cysteines.

176. The composition of claim 172 wherein the chemically or enzymatically oxidized synthetic CC10 further comprises carbonyl groups in excess of those present in unmodified CC10.

177. The composition of claim 172 wherein the chemically or enzymatically oxidized synthetic CC10 further comprises one or more hydroxyprolines.

178. The composition of claim 172 wherein the chemically or enzymatically oxidized synthetic CC10 further comprises one or more α-aminoadipic semialdehydes, chloramines, MDA-Lys, HNE-Lys, acrolein-Lys, carboxymethyllysines, or pHA-Lys.

179. The composition of claim 172 wherein the chemically or enzymatically oxidized synthetic CC10 further comprises one or more 2-amino-3-ketobutyric acids, chloramines, valine peroxides, leucine peroxides, oxalic acids, or pyruvic acids.

180. The composition of claim 172 wherein the chemically or enzymatically oxidized synthetic CC10 further comprises one or more labels, chemicals, lipids, or peptides attached to a glutamine or lysine residue.

* * * * *

SEQUENCE LISTING

<160> NUMBER OF SEQ ID NOS: 8

<210> SEQ ID NO 1
<211> LENGTH: 70
<212> TYPE: PRT
<213> ORGANISM: Homo sapiens

<400> SEQUENCE: 1

Glu Ile Cys Pro Ser Phe Gln Arg Val Ile Glu Thr Leu Leu Met Asp
1               5                   10                  15

Thr Pro Ser Ser Tyr Glu Ala Ala Met Glu Leu Phe Ser Pro Asp Gln
            20                  25                  30

Asp Met Arg Glu Ala Gly Ala Gln Leu Lys Lys Leu Val Asp Thr Leu
        35                  40                  45

Pro Gln Lys Pro Arg Glu Ser Ile Ile Lys Leu Met Glu Lys Ile Ala
    50                  55                  60

Gln Ser Ser Leu Cys Asn
65                  70

<210> SEQ ID NO 2
<211> LENGTH: 86
<212> TYPE: PRT
<213> ORGANISM: Homo sapiens

<400> SEQUENCE: 2

Ala Ala Phe Leu Val Gly Ser Ala Lys Pro Val Ala Gln Pro Val Ala
1               5                   10                  15

Ala Leu Glu Ser Ala Ala Glu Ala Gly Ala Gly Thr Leu Ala Asn Pro
            20                  25                  30

Leu Gly Thr Leu Asn Pro Leu Lys Leu Leu Leu Ser Ser Leu Gly Ile
        35                  40                  45

Pro Val Asn His Leu Ile Glu Gly Ser Gln Lys Cys Val Ala Glu Leu
    50                  55                  60

Gly Pro Gln Ala Val Gly Ala Val Lys Ala Leu Lys Ala Leu Leu Gly
65                  70                  75                  80

Ala Leu Thr Val Phe Gly
                85

<210> SEQ ID NO 3
<211> LENGTH: 73
<212> TYPE: PRT
<213> ORGANISM: Homo sapiens

<400> SEQUENCE: 3

Ala Phe Leu Ile Asn Lys Val Pro Leu Pro Val Asp Lys Leu Ala Pro
1               5                   10                  15

Leu Pro Leu Asp Asn Ile Leu Pro Phe Met Asp Pro Leu Lys Leu Leu
            20                  25                  30

Leu Lys Thr Leu Gly Ile Ser Val Glu His Leu Val Glu Gly Leu Arg
        35                  40                  45

Lys Cys Val Asn Glu Leu Gly Pro Glu Ala Ser Glu Ala Val Lys Lys
    50                  55                  60

Leu Leu Glu Ala Leu Ser His Leu Val
65                  70

<210> SEQ ID NO 4
<211> LENGTH: 95
<212> TYPE: PRT
<213> ORGANISM: Homo sapiens

<400> SEQUENCE: 4

Ser Gly Cys Lys Leu Leu Glu Asp Met Val Glu Lys Thr Ile Asn Ser
1               5                   10                  15

Asp Ile Ser Ile Pro Glu Tyr Lys Glu Leu Leu Gln Glu Phe Ile Asp
            20                  25                  30

Ser Asp Ala Ala Glu Ala Met Gly Lys Phe Lys Gln Cys Phe Leu
        35                  40                  45

Asn Gln Ser His Arg Thr Leu Lys Asn Phe Gly Leu Met Met His Thr
    50                  55                  60

Val Tyr Asp Ser Ile Trp Cys Asn Met Lys Ser Asn Met Lys Leu Leu
65                  70                  75                  80

Met Val Leu Met Leu Ala Ala Leu Leu Leu His Cys Tyr Ala Asp
                85                  90                  95

<210> SEQ ID NO 5
<211> LENGTH: 93
<212> TYPE: PRT
<213> ORGANISM: Homo sapiens

<400> SEQUENCE: 5

Ser Gly Cys Pro Leu Leu Glu Asn Val Ile Ser Lys Thr Ile Asn Pro
1               5                   10                  15

Gln Val Ser Lys Thr Glu Tyr Lys Glu Leu Leu Gln Glu Phe Ile Asp
            20                  25                  30

Asp Asn Ala Thr Thr Asn Ala Ile Asp Glu Leu Lys Glu Cys Phe Leu
        35                  40                  45

Asn Gln Thr Asp Glu Thr Leu Ser Asn Val Val Phe Met Gln Leu
    50                  55                  60

Ile Tyr Asp Ser Ser Leu Cys Asp Leu Phe Met Lys Leu Leu Met Val
65                  70                  75                  80

Leu Met Leu Ala Ala Leu Ser Gln His Cys Tyr Ala Gly
                85                  90

<210> SEQ ID NO 6
<211> LENGTH: 90
<212> TYPE: PRT
<213> ORGANISM: Homo sapiens

<400> SEQUENCE: 6

Val Val Cys Gln Ala Leu Gly Ser Glu Ile Thr Gly Phe Leu Leu Ala

```
                1               5                   10                  15
Gly Lys Pro Val Phe Lys Phe Gln Leu Ala Lys Phe Lys Ala Pro Leu
                20                  25                  30

Glu Ala Val Ala Ala Lys Met Glu Val Lys Lys Cys Val Asp Thr Met
            35                  40                  45

Ala Tyr Glu Lys Arg Val Leu Ile Thr Lys Thr Leu Gly Lys Ile Ala
    50                  55                  60

Glu Lys Cys Asp Arg Met Arg Leu Ser Val Cys Leu Leu Leu Leu Thr
65                  70                  75                  80

Leu Ala Leu Cys Cys Tyr Arg Ala Asn Ala
                85                  90

<210> SEQ ID NO 7
<211> LENGTH: 90
<212> TYPE: PRT
<213> ORGANISM: Homo sapiens

<400> SEQUENCE: 7

Glu Phe Cys Pro Ala Leu Val Ser Glu Leu Leu Asp Phe Phe Phe Ile
1               5                   10                  15

Ser Glu Pro Leu Phe Lys Leu Ser Leu Ala Lys Phe Asp Ala Pro Pro
                20                  25                  30

Glu Ala Val Ala Ala Lys Leu Gly Val Lys Arg Cys Thr Asp Gln Met
            35                  40                  45

Ser Leu Gln Lys Arg Ser Leu Ile Ala Glu Val Leu Val Lys Ile Leu
    50                  55                  60

Lys Lys Cys Ser Val Met Lys Leu Ser Val Cys Leu Leu Leu Val Thr
65                  70                  75                  80

Leu Ala Leu Cys Cys Tyr Gln Ala Asn Ala
                85                  90

<210> SEQ ID NO 8
<211> LENGTH: 83
<212> TYPE: PRT
<213> ORGANISM: Homo sapiens

<400> SEQUENCE: 8

Leu Cys Cys Tyr Gln Ala His Ala Leu Val Cys Pro Ala Val Ala Ser
1               5                   10                  15

Glu Ile Thr Val Phe Leu Phe Leu Ser Asp Ala Ala Val Asn Leu Gln
                20                  25                  30

Val Ala Lys Leu Asn Pro Pro Pro Glu Ala Leu Ala Ala Lys Leu Glu
            35                  40                  45

Val Lys His Cys Thr Asp Gln Ile Ser Phe Lys Lys Arg Leu Ser Leu
    50                  55                  60

Lys Lys Ser Trp Trp Lys Met Arg Leu Ser Val Cys Leu Leu Met Val
65                  70                  75                  80

Ser Leu Ala
```